United States Patent [19]

Shiratsuchi et al.

[11] 4,374,840
[45] Feb. 22, 1983

[54] CERTAIN PHENYL OR PYRIDYL-PROPANOL-AMINES CONTAINING ALKYL-NITRATE MOIETIES

[75] Inventors: Masami Shiratsuchi, Musashimurayama; Noboru Shimizu, Higashimurayama; Hiromichi Shigyo, Fuchu; Yoshinori Kyotani, Higashiyamato; Hisashi Kunieda, Higashimurayama; Kiyoshi Kawamura, Tokorozawa; Seiichi Sato; Toshihiro Akashi, both of Higashimurayama; Masahiko Nagakura, Sayama; Naotoshi Sawada, Kawasaki; Yasumi Uchida, Ichikawa, all of Japan

[73] Assignee: Kowa Company, Ltd., Aichi, Japan

[21] Appl. No.: 233,643

[22] Filed: Feb. 11, 1981

[30] Foreign Application Priority Data

Feb. 13, 1980 [JP] Japan .................................. 55-15433

[51] Int. Cl.³ .................. A61K 31/44; A61K 31/135; C07D 213/74
[52] U.S. Cl. .................................. 424/263; 424/330; 546/296; 546/297; 546/300; 564/349; 564/355; 564/165; 564/86
[58] Field of Search ................ 564/349; 546/297, 296, 546/300; 424/263, 330

[56] References Cited

U.S. PATENT DOCUMENTS 4,065,461 12/1977 Ross-Petersen ..................... 424/263

Primary Examiner—Alan L. Rotman

Attorney, Agent, or Firm—Wenderoth, Lind & Ponack

[57] ABSTRACT

A compound represented by the following formula

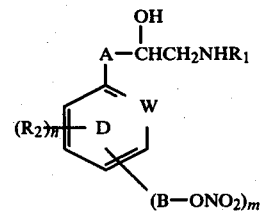

wherein
A represents a direct bond or the bond $-O-CH_2-$,
B represents a $C_1-C_{11}$ alkylene group bonded to a carbon atom of the aromatic ring D either directly or through $-O-$, $-S-$, $-SO-$ or $-NH-$,
W represents a carbon or nitrogen atom,
$R_1$ represents a $C_3-C_7$ alkyl group, a hydroxy-$C_1-C_6$ alkyl group, or a phenyl- or diphenyl-alkyl group with the alkyl group having 1 to 4 carbon atoms,
$R_2$ represents a member selected from the group consisting of hydrogen, halogen, OH, $C_1-C_4$ alkyl, $NO_2$, $C_1-C_4$ alkoxy, acetyl, allyloxy, carbamoyl and sulfamoyl, and when two or more $R_2$ groups exist, they may be identical or different, and
n represents 1, 2 or 3 and m represents 1 or 2, provided that $n+m \geq 4$;

and an acid addition salt thereof; a process for producing the same; and a pharmaceutical composition comprising aforesaid compound.

3 Claims, No Drawings

CERTAIN PHENYL OR PYRIDYL-PROPANOL-AMINES CONTAINING ALKYL-NITRATE MOIETIES

This invention relates to pharmaceutically useful aromatic aminoethanol compounds having various pharmacological activities such as vascular smooth muscle relaxing action, adrenergic α- and β-blocking action resulting in a reduction in heart beat rate, myocardial oxygen consumption reducing action, blood flow increasing action and blood pressure lowering action. The invention also relates to a process for production of the aforesaid compounds and to a use of these compounds.

The compounds of this invention have not been described in the literature and are therefore novel. They can be represented by the following formula (I).

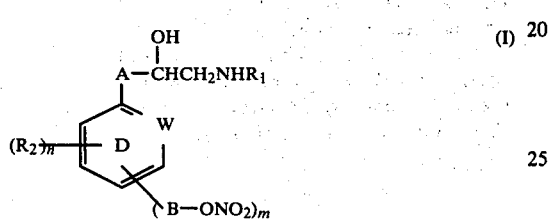

wherein

A represents a direct bond or the bond —O—CH$_2$—,

B represents a C$_1$–C$_{11}$ alkylene group bonded to a carbon atom of the aromatic ring D either directly or through —O—, —S—, —SO— or —NH—, W represents a carbon or nitrogen atom, R$_1$ represents a C$_3$–C$_7$ alkyl group, a hydroxy-C$_1$–C$_6$ alkyl group, or a phenyl- or diphenyl-alkyl group with the alkyl group having 1 to 4 carbon atoms, R$_2$ represents a member selected from the group consisting of hydrogen, halogen, OH, C$_1$–C$_4$ alkyl, NO$_2$, C$_1$–C$_4$ alkoxy, acetyl, allyloxy, carbamoyl and sulfamoyl, and when two or more R$_2$ groups exist, they may be identical or different, and n represents 1, 2 or 3 and m represents 1 or 2, provided that n+m≧4.

The compounds of the invention also embrace the acid addition salts of the compounds of formula (I), preferably their pharmaceutically acceptable acid addition salts.

As a result of extensive work on aromatic aminoethanol compounds and their synthesis and ultilization, the present inventors have succeeded in synthesizing the novel compounds of formula (I) and the acid addition salts thereof which have not previously been described in the literature. Their work has also led to the discovery that these novel compounds have various pharmacological effects which make them useful for the treatment of cardiovascular diseases.

German DOS Nos. 2804625 and 2805404, European Patent Laid-Open Publication No. 3278, and Japanese Laid-Open Patent Publication No. 149937/1978, for example, disclose compounds having adrenergic β-blocking action. The compounds disclosed in the prior art, however, are clearly distinguished from the compounds of the present invention in that the prior art compounds do not have the group ←B—ONO$_2$)$_m$ shown in the above general formula (I). They also differ from each other in pharmacological efficacy in that while the prior art compounds do not show blood pressure lowering action and blood flow increasing action, the compounds of the invention represented by formula (I) exhibit these actions as well.

It is an object of this invention therefore to provide novel compounds of general formula (I).

Another object of this invention is to provide a pharmaceutical use of the compounds of formula (I).

Still another object of this invention is to provide a process for producing the compounds of formula (I).

The above and other objects and advantages of the invention will become apparent from the following description.

The compounds (I) of this invention can be produced, for example, by the following processes.

Process (A)

A compound of the following formula

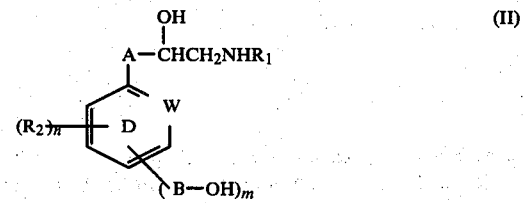

wherein A, B, W, R$_1$, R$_2$, n and m are as defined above, is subjected to a nitrate ester-forming reaction.

Process (B)

A compound of the following formula

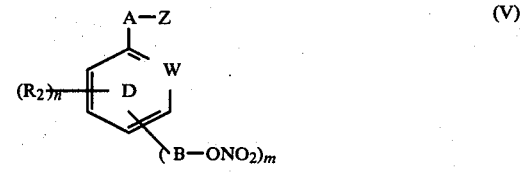

wherein
Z represents

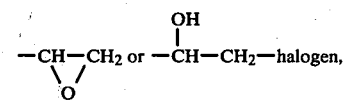

and A, B, W, R$_2$, n and m are as defined above, is reacted with an amine of the following formula

NH$_2$R$_1$ wherein R$_1$ is as defined above.

Process (C)

A compound of the following formula

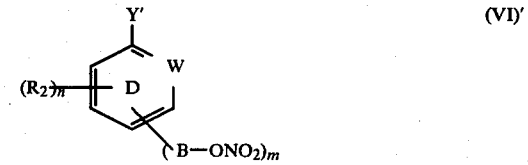

wherein Y' represents a hydroxyl group, a haloacetyl group, a tosyloxy group or a halogen atom, and B, W, R2, n and m are as defined hereinabove, provided that W is a carbon atom when Y' is a hydroxyl group, and a nitrogen atom when Y' is a tosyloxy or halogen atom, is reacted with (i) an oxazolidine of the following formula

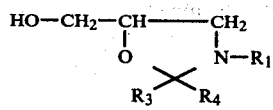

(VIII)

wherein R1 is as defined above, and R3 and R4, independently from each other, represent a hydrogen atom or a phenyl group, when Y' is a tosyloxy group or a halogen atom and W is a nitrogen atom in formula (VI)'; or (ii) an oxazolidine of the following formula

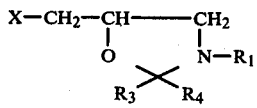

(IX)

wherein X represents a tosyloxy group or a halogen atom, and R1, R3 and R4 are as defined, when Y' is a hydroxyl group and W is a carbon atom in formula (VI).

The compounds of formula (II), (V) and (VI) in processes (A), (B) and (C) may, for example, be prepared from compounds of the following formula

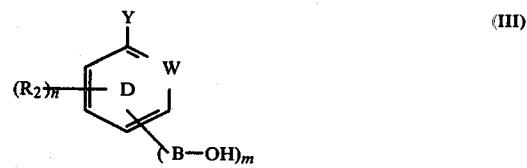

(III)

wherein Y represents hydroxyl, ethoxycarbonyloxy, acetyl, haloacetyl, tosyloxy or halogen, and B, W, R2, n and m are as defined above, by utilizing aminoalkanol-forming reaction, amination, nitrate ester-forming reaction, glycidyl-forming reaction, epoxidation, halohydrin-forming reaction, etc.

The following scheme shows several embodiments of producing the compound (I) of this invention including the production of the starting compounds (II), (V) and (VI) from the compound (III).

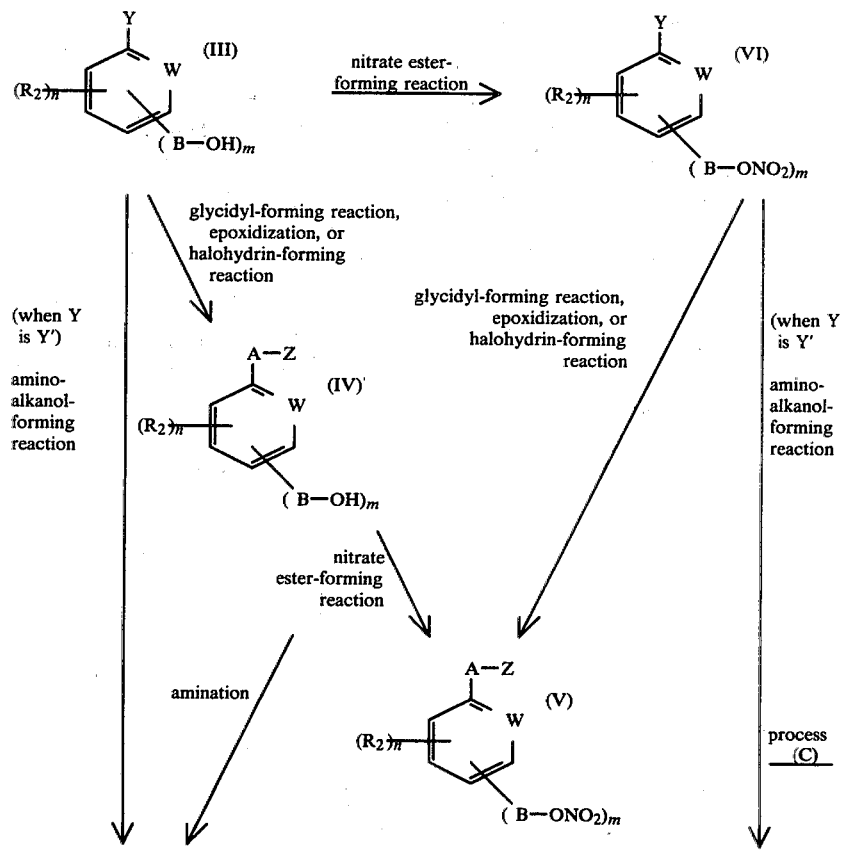

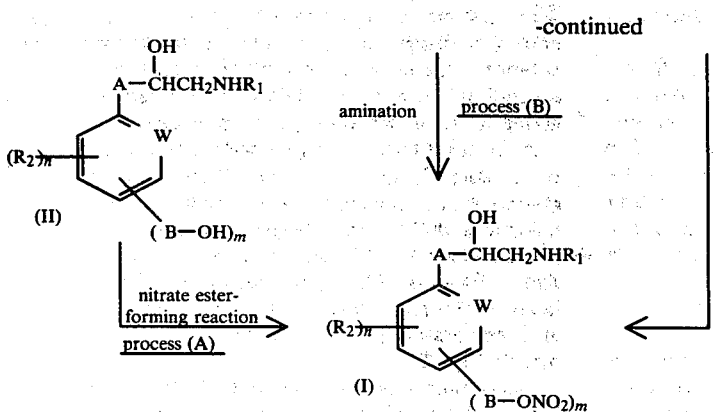

As is schematically shown above, the compound of formula (II) used in process (A) can be obtained by subjecting the compound of formula (III) directly to aminoalkanol-forming reaction (provided that Y in formula (III) is Y' as described with respect to process (C)), or by aminating the compound of formula (IV) which may be obtained by subjecting the compound of formula (III) to glycidyl-forming reaction, epoxidation or halohydrin-forming reaction. The compound of formula (V) used in process (B) can be obtained by subjecting the compound of formul (IV) obtained as above to nitrate ester-forming reaction, or by subjecting the compound of formula (VI), which can be obtained by subjecting the compound of formula (III) to nitrate ester-forming reaction, to glycidyl-forming reaction, epoxidation or halohydrin-forming reaction. The compound of formula (VI)' used in process (C) can be obtained by subjecting the compound of formula (III) in which Y is Y' to nitrate ester-forming reaction.

The nitrate ester-forming reaction, amination, and aminoalkanol-forming reaction in the production of the starting compounds (II), (V) and (VI) can be carried out in the same way as in these reactions in processes (A), (B) and (C). The reactions are specifically illustrated below.

1. Nitrate ester-forming reaction

The nitrate ester-forming reaction of the compounds of formulae (II), (III) and (IV) can be carried out by contacting the compound of formula (II), (III) or (IV) with a nitrate-ester forming reaction such as fuming nitric acid, or a mixture of it with acetic anhydride, or a mixture of fuming nitric acid and sulfuric acid at a relatively low temperature in the presence or absence of a solvent. For example, the reaction is carried out at a temperature of from about −40° C. to room temperature for about 1 minute to about 1 hour.

Alternatively, this reaction can be performed by halogenating the hydroxyl group of the group B—OH in the compound of formula (II), (III) or (IV), and contacting the product with silver nitrate. The reaction can be carried out, for example, at a temperature of from room temperature to about 90° C. for about 1 to about 10 hours. The halogenation may be performed by heating the compound with an alkali halide in dimethyl formamide, following mesylation or tosylation.

The solvent used in the above reaction is an inert organic solvent such as acetonitrile, dioxane or tetrahydrofuran.

The mole ratios of the reactants can be selected as desired. In the first-mentioned embodiment, the reagents is used in an amount of about 1 to about 10 moles per mole of the compound of formula (II), (III), or (IV). In the latter, the silver nitrate is used in an amount of about 2 to about 10 moles per mole of the halogenated product.

2. Epoxidation, glycidyl-forming reaction or halohydrin-forming reaction

When in the compound of formula (III) or (IV), Y is a hydroxyl group and another hydroxyl group is present in it, the compound of formula (IV) or (V) in which the group A-Z is a glycidyl or halohydrin group can be prepared by protecting hydroxyl groups other than Y by means known per se, and contacting the compound with an epihalohydrin in the presence of a base. This reaction can be carried out for example at a temperature of about 10° to about 70° C. for a period of about 0.5 hour to about 20 hours. Protection of the hydroxyl groups can be effected, for example, by adding 2,3-dihydro-4H-pyran in the presence of an acid catalyst to conver it to a tetrahydropyranyl ether, or by reacting the compound with benzyl chloride or benzyl bromide to convert it to a benzyl ether.

When the compound (IV) obtained in this manner is to be converted to the compound of formula (V) by nitrate ester-forming reaction, the protecting group may be split off by, for example, acid hydrolysis to use it as the compound of formula (IV). When the route of (IV)→(II)→(I) is utilized, the protecting group is split off in the same way as above before or after performing the aminating step. When the route of (V)→(I) is used, the protecting group is also split off in the same way as above before or after the aminating step.

According to another embodiment, when Y in the compound of formula (III) or (VI) is a haloacetyl group, a compound of formula (IV) or (V) n in which Z is an epoxy group may be easily produced by reducing the above compound with a reducing agent to form the corresponding halohydrin, and reacting the product with an alkali such as sodium hydroxide, potassium hydroxide or triethylamine. This reaction can be carried out, for example, at a temperature of from about 0° C. to room temperature for a period of about 1 minute to about 1 hour.

In these embodiments, a solvent is not required. But if desired, it may be used. Examples are inert organic solvents such as methanol, ethanol, dioxane and tetrahydrofuran. Examples of the base used in the former embodiment include inorganic or organic bases such as sodium hydroxide, potassium hydroxide and triethylamine. In the latter embodiment, examples of the reducing agent include sodium borohydride and lithium aluminum hydride.

The mole proportions of the reactants may be selected as desired. In the former embodiment, about 1 to about 10 moles of the epihalohydrin can be used per mole of the compound of formula (III) or (VI), and in the latter embodiment about 1 to about 5 moles of the reducing agent may be used per mole of the compound of formula (III) or (VI). The amount of the base used in the first-mentioned embodiment is from about 1 to about 10 moles.

3. Amination reaction

The amination for converting the compound of formula (IV) or (V) to the compound of formula (II) or (I) may be carried out, for example, by reacting the compound of formula (IV) or (V) in which Z is an epoxy group with an amine of the formula $NH_2R_1$ (in which $R_1$ is as defined above) in the presence of a solvent. The reaction may be carried out, for example, at a temperature of from room temperature to about 90° C. for a period of about 1 minute to about 1 hour.

According to another embodiment, the amination may be performed by reacting the compound of formula (IV) or (V) in which Z is a halohydrin group with an amine of the formula $NH_2R_1$ (in which $R_1$ is as defined above) in the presence of a solvent in a sealed pipe at a temperature of, for example, about 50° to about 150° C. for a period of about 10 minutes to about 3 hours.

In any of the above embodiments, an inert solvent such as water, methanol, ethanol or benzene may be used as the solvent.

The mole proportions of the reactants may be selected as desired. For example, about 2 to about 100 moles of the amine can be used per mole of the compound of formula (IV) or (V).

4. Aminoalkanol-forming reaction

A compound of formula (III) or (VI) in which Y is Y', that is, a compound in which Y' is a haloacetyl group, or a compound in which Y' is a hydroxyl group, a tosyloxy group or a halogen atom and W is a carbon atom when Y' is hydroxyl and a nitrogen atom when Y' is tosyloxy or halogen, can be converted to the compound of formula (I) or (II) by aminoalkanol-forming reaction.

When the compound of formula (II) or (VI) in which Y' is a haloacetyl group contains a hydroxyl group, it is protected in the manner described above with regard to the reaction 2, and the protected compound is reacted with the amine $NH_2R_1$. Reduction of the aminoacetyl compound gives the compound of formula (I) or (II). Deprotection may be carried out by acid hydrolysis.

In this embodiment, the reaction with the amine may be performed in an inert organic solvent such as methyl ethyl ketone for about 1 to 5 hours under refluxing temperature conditions. The rlesulting aminoacetyl compound may be reduced by using a reducing agent, or by using a catalytic reducing technique. Examples of the reducing agent are lithium aluminum hydride, sodium borohydride and aluminum borohydride. Palladium-carbon and other noble metal-containing reducing catalysts may, for example, be used in the catalytic reduction.

The reduction with a reducing agent may be carried out in an inert organic solvent such as tetrahydrofuran, ether or dioxane at a temperature of about 0° C. to about 100° C. for a period of about 1 hour to about 5 hours.

The catalytic reduction may be performed in the presence of hydrogen using the above-exemplified reducing catalyst in the presence of a solvent such as methanol or ethanol at a temperature of from room temperature to about 50° C. under atmospheric pressure.

According to a second embodiment, the compound of formula (I) or (II) can be obtained by reacting a compound of formula (VI)' in which Y' is tosyloxy or halogen and W is nitrogen or a compound of formula (III) in which Y is Y' mentioned above with the oxazolidine of formula (VIII). The reaction may be carried out in an inert organic solvent such as dimethyl formamide at a temperature of, for example, from room temperature to 150° C.

According to a third embodiment, the compound of formula (I) or (II) may be obtained by reacting a compound of formula (VI)' in which Y' is hydroxyl and W is carbon or a compound of formula (III) in which Y is Y' mentioned above with the oxazolidine of formula (IX). The reaction may be carried out in an inert organic solvent such as dimethyl formamide at a temperature of, for example, 20° C. to 120° C.

The compound of formula (I) of this invention can be obtained by properly selecting the above processes. The compounds of formula (I) which can be so obtained have various pharmacological activities including vascular smooth muscle relaxing action, adrenergic $\alpha$- and $\beta$-blocking action resulting in a reduction in heart beat rate, myocardial oxygen consumption reducing action, blood flow increasing action and blood pressure lowering action. Because of these pharmacological activities, these compounds are useful as medicines for treatment of cardiovascular diseases, such as anti-anginal drugs, hypotensive agents, improvers for the cardiovascular system, and antiarrhythmic drugs.

Thus, according to this invention, there is provided a pharmaceutical composition comprising an amount, effective for treatment of cardiovascular diseases, of a compound of the following formula (I) or a pharmaceutically acceptacle acid addition salt thereof, and a pharmaceutically acceptable diluent or carrier.

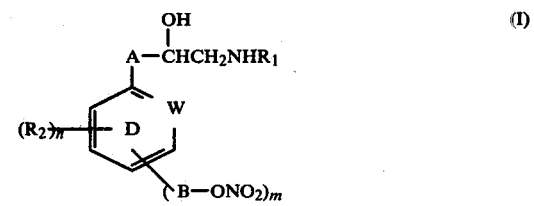

wherein

A represents a direct bond or the bond —O—$CH_2$—,

B represents a $C_1$–$C_{11}$ alkylene group bonded to a carbon atom of the aromatic ring D either directly or through —O—, —S—, —SO— or —NH—, W represents a carbon or nitrogen atom, $R_1$ represents a $C_3$–$C_7$ alkyl group, a hydroxy-$C_1$–$C_6$ alkyl group, or a phenyl- or diphenyl-alkyl group with the alkyl group having 1 to 4 carbon atoms, $R_2$ represents a member selected from the group consisting of hydrogen, halogen, OH, $C_1$–$C_4$ alkyl, $NO_2$, $C_1$–$C_4$ alkoxy, acetyl, allyloxy, carbamoyl and sulfamoyl, and when two or more $R_2$ groups exist, they may be identical or different, and n represents 1, 2 or 3 and m represents 1 or 2, provided that $n+m \geq 4$ The cardiovascular disease treating agent having all of the aforesaid pharmacological activities has not been known heretofore. Moreover, the unique pharmacological activities of the compound of formula (I) are long-lasting, and the absorption of this compound in vivo in oral administration is excellent. Furthermore, this compound has low toxicity. Hence, this pharmaceutical composition is useful for prevention and treatment of diseases of the cardiovascular system.

The compound may be in the form of its acid addition salt. The addition salt can be easily obtained by contacting the compound of formula (I) with a suitable inorganic or organic acid. Those acid addition salts which are pharmaceutically acceptable are preferred. Examples of the acid addition salts are hydrochlorides, nitrates, sulfates, phosphates, oxalates, maleates, methanesulfonates, ethanesufonates, p-toluenesulfonates, fumarates, malonates and acetates.

Liquid or solid carriers or diluents may be used in forming the pharmaceutical composition of this invention. They may include excipients, binders, lubricants, emulsifiers, etc. Known in pharmaceutical preparation. Examples of these carriers or diluents include starches such as potato starch, wheat starch, corn starch and rice starch; sugars such as lactose, sucrose, glucose, mannitol and sorbitol; celluloses such as crystalline cellulose, carboxy methyl cellulose calcium and hydroxypropyl cellulose of a low degree of substitution; inorganic substances such as potassium phosphate, calcium sulfate, calcium carbonate and talc; binder compounds such as gelatin, gum arabic, methyl cellulose, carboxy methyl cellulose sodium, polyvinyl pyrrolidone and hydroxypropyl cellulose; polyhydric alcohol ester-type nonionic surfactants such as fatty acid monoglycerides, sorbitan fatty acid esters, sucrose and polyglycerol fatty acid esters; and polyoxyethylene-type nonionic surfactants.

The pharmaceutical compositions may be in any known dosage forms known in the art of formulating pharmaceuticals, such as suppositories, powders, granules, tablets, sublingual tablets, liquid preparations, injectable preparations, and suspensions.

The pharmaceutical composition of this invention may be administered by any of peroral or parenteral routes, such as intravenous, sublingual or intrarectal administration. For long-term administration, the oral route is preferred.

The dose may be changed as desired. For example, the compound of formula (I) may be administered in a dose of about 1 to about 100 mg/body/day, preferably about 5 to about 50 mg/body/day. The compounds of this invention have extremly low toxicity as shown by their acute toxicity ($LD_{50}$) of 800 to 1500 mg/kg (mouse, oral) and 80 to 120 mg/kg (mouse, intravenous).

Some examples are given below for testing the pharmacological efficacy of the compounds of this invention.

Test [I]

Adult dogs were anesthetized by intravenous administration of 30 mg/kg of pentobarbital, and examined under artificial respiration for the action of the compound of this invention on blood pressure and heart rate.

Measuring method:
(1) Blood pressure
A catheter was inserted into the femoral artery, and connected to a pressure transducer for measurement of the blood pressure.

(2) Heart rate
Measured by pulse pressure changes.
Dose and Method of Administration:
The test drug was dissolved in 0.1 N hydrochloric acid, and administered intravenously in a dose of 20 μg/kg.

The results of the test are shown in Table 1. The numbered compounds in the following tables correspond to the compounds obtained in the correspondingly numbered Examples given hereinbelow.

TABLE 1

| Compound No. | Reduction in blood pressure | Reduction in heart rate |
| --- | --- | --- |
| 2 | + + | + + |
| 6 | + + + (*) | + + + |
| 7 | + + | + + + |
| 23 | + + | + + + |
| 33 | + + (*) | + + |
| 50 | + + + | + + + |
| 55 | + + | + + + |
| 61 | + + + | + + + |
| 62 | + + + | + + |
| 63 | + + + | + + + |

Score
+: a reduction of less than 20%
+ +: a reduction of 20 to 50%
+ + +: a reduction of more than 50%
(*): The hypotensive action is especially longlasting.

The results shown in Table 1 demonstrate that the compounds of the present invention have long-lasting hypotensive action, and an action of decreasing heart rate.

Test [II]

The isolated atrial muscle of a guinea pig was used, and its contractile force and heart rate were recorded. Thus, the antagonistic action of the test drug against isoproterenol was examined. The drug was used in a concentration of $10^{-9}$ to $4\times10^{-4}$ mole. As a control drug, propranolol hydrochloride was used.

Results:
The compounds Nos. 3, 4, 8, 13, 14, 15 and 17 had the same degree of action as the control drug.
These results suggest that the compounds of this invention have the same degree of β-blocking action as propranolol hydrochloride.

Test [III]

Mongrel dogs were anesthetized by intravenous administration of 30 mg/kg of pentobarbital, and examined under artifical respiration for the following items.
(1) Left ventricular end diastolic pressure (LVEDP)
Measured by advancing a catheter transducer to the left ventricle.
(2) Coronary blood flow
Measured by setting an electro magnetic flow meter probe in the left circumflex branch.
(3) Common carotid blood flow
Measured by setting an electromagnetic flow probe at the common carotid artery.
Dose and Method of Administration:
Each of the compounds shown in Tables 2 to 4 was dissolved in 0.1 N hydrochloric acid, and intravenously administered in a dose of 20 μg/kg.
The results are shown in Tables 2 to 4.

TABLE 2

| Compound No. | Decrease rate (%) in LVEDP (1) |
|---|---|
| 1 | ↓↓↓ |
| 6 | ↓↓ |
| 7 | ↓↓↓ |
| 23 | ↓↓ |
| 33 | ↓ |
| 50 | ↓↓ |
| 62 | ↓ |

Score
↓↓↓ : a decrease of more than 40%
↓↓ : a decrease of 20 to 40%
↓ : a decrease of less than 20%

TABLE 3

| Compound No. | Increase rate (%) in coronary flow (2) |
|---|---|
| 2 | ↑↑ |
| 6 | ↑↑ |
| 7 | ↑↑ |
| 26 | ↑ |
| 32 | ↑ |
| 33 | ↑ |
| 34 | ↑ |

Score
↑↑ : an increase of more than 30%
↑ : an increase of 30% or less

TABLE 4

| Compound No. | Increase rate (%) in flow in the common carotid artery (3) |
|---|---|
| 6 | ↑↑ |
| 7 | ↑↑ |
| 26 | ↑ |
| 33 | ↑ |
| 34 | ↑ |
| 61 | ↑ |

Score
↑↑ : an increase of more than 30%
↑ : an increase of 30% or less

These results suggested that the compounds of this invention have pharmaceutical actions different from conventional β-blockers.

Drug formulation example

Some typical examples of drug formulation using the compounds of this invention are shown below. All parts are by weight.

| (a) Tablet | |
|---|---|
| Compound (I) of the invention | 6 parts |
| Crystalline cellulose | 50 parts |
| Lactose | 34 parts |
| Carboxy methyl cellulose calcium | 9 parts |
| Magnesium stearate | 1 part |

The above ingredients were mixed uniformly, and tableted by a direct tableting method into tables each having a diameter of 5 mm and a weight of 50 mg. The tablets obtained showed a hardness of 6 kg and a disintegration time of 1 minute.

| (b) Granules | | |
|---|---|---|
| (1) | Compound (I) of the invention | 1 part |
| | Lactose | 40 parts |
| | Crystalline cellulose | 25 parts |
| | Corn starch | 32 parts |
| (2) | Hydroxy propyl cellulose | 2 parts |
| | Ethanol | 25 parts |

The ingredients in (1) were uniformly mixed, and then a solution consisting of the ingredients in (2) was added, and they were kneaded. The mixture was granulated by an extrusion granulating method, dried in vacuum at 50° C., and then sieved to form granules.

| (c) Fine particles | |
|---|---|
| Compound (I) of the invention | 2 parts |
| Crystalline cellulose | 20 parts |
| Lactose | 50 parts |
| White sucrose | 26 parts |
| Hydroxypropyl cellulose | 2 parts |

The above ingredients were uniformly mixed, and 25 parts of ethanol was added, followed by kneading. The kneaded mixture was granulated by a pulverizing-granulating method, dried by sending air at 50° C., and then sieved to produced fine particles.

| (d) Capsules | |
|---|---|
| Compound (I) of the invention | 10 parts |
| Lactose | 40 parts |
| Crystalline cellulose | 30 parts |
| Talc | 10 parts |

The above ingredients were uniformly mixed, and filled in an amount of 90 mg in each of #5 lock capsules to form capsular preparations.

The following Examples illustrate the production of the compounds (I) of the invention.

EXAMPLE 1

1-iso-Propylamino-3-[3-(2-nitratoethoxy)phenoxy]-2-propanol of the formula:

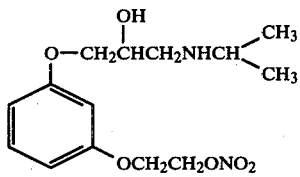

3.0 g of 2-[(3-ethoxycarbonyloxy)phenoxy]ethanol was dissolved in 60 ml of acetonitrile, and the solution was cooled to below 0° C. With stirring, a mixture of 2.72 g of acetic anhydride and 1.7 g of fuming nitric acid was added dropwise. After the addition, the mixture was stirred for 10 minutes. The reaction solution was poured into an aqueous solution of sodium hydrogen carbonate, and then extracted with ethyl acetate. The extract was washed with an aqueous solution of sodium chloride and dried. When ethyl acetate was distilled off under reduced pressure, 3.43 g of a crude product was obtained. The crude product was chromatographed on a silica gel column to afford 2.45 g (yield 68.1%) of 2-[(3-ethoxycarbonyloxy)phenoxy]ethyl nitrate.

3.0 g of the resulting 2-[(3-ethoxycarbonyloxy)-phenoxy]ethyl nitrate was dissolved in 50 ml of methanol, and with ice cooling, 13 ml of a 1 N aqueous solution of sodium hydroxide was added. The mixture was stirred for 15 minutes, and thereafter, the mixture was neutralized with acetic acid and evaporated to dryness under reduced pressure. The residue was extracted with ethyl acetate. The extract was successively washed with an aqueous solution of sodium hydrogen carbonate and an aqueous solution of sodium chloride and dried. Subsequent distillation of the solvent afforded 2.13 g (yield 96.8%) of 2-[(3-hydroxy)phenoxy]ethyl nitrate.

1.7 g of the resulting 2-[(3-hydroxy)phenoxy]-ethyl nitrate and 2.36 g of epichlorohydrin were dissolved in a mixture of 26 ml of 1 N sodium hydroxide and 34 ml of dioxane, and the solution was stirred at 50° C. for 1 hour. After the reaction, the reaction mixture was dried under reduced pressure, and the residue was extracted with ethyl acetate. The extract was washed with an aqueous solution of sodium chloride and dried, and the solvent was distilled off. The residue was chromatographed on a silica gel column to afford 1.2 g (yield 55.5%) of 1,2-epoxy-3-[3-(2-nitratoethoxy)phenoxy]-propane.

0.4 g of the resulting 1,2-epoxy-3-[3-(2-nitratoethoxy)phenoxy]propane was dissolved in 30 ml of ethanol, and 10 ml of isopropyl amine was added. The mixture was boiled for 15 minutes under reflux. After the reaction, the solvent was distilled off under reduced pressure to afford 0.49 g (yield 100%) of 1-isopropylamino-3-[3-(2-nitratoethoxy)phenoxy]-2-propanol as a pale yellow viscous oil.

Elemental analysis for $C_{14}H_{22}N_2O_6$:

| | C | H | N |
|---|---|---|---|
| Calculated (%): | 53.49 | 7.05 | 8.91 |
| Found (%): | 53.51 | 7.10 | 8.85 |

NMR spectrum ($\delta$, $CDCl_3$):

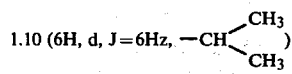

1.10 (6H, d, J=6Hz, —CH(CH$_3$)(CH$_3$))

4.23 (2H, t, J=5Hz, —OCH$_2$CH$_2$ONO$_2$)
4.80 (2H, t, J=5Hz, —OCH$_2$CH$_2$ONO$_2$)
6.30–7.30 (4H, m, H of the aromatic ring)
IR spectrum ($v_{max}^{liquid\,film}$ cm$^{-1}$): 1620, 1280 (—NO$_2$).

EXAMPLE 2

1-iso-Propylamino-3-[2-(2-nitrotoethoxy)phenoxy]-2-propanol of the formula:

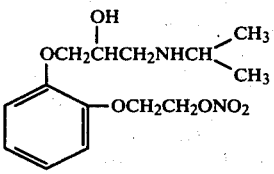

69 ml of 1 N sodium hydroxide and 7.3 ml of epichlorohydrin were added to a solution of 7.2 g of 2-(2-hydroxyphenoxy)ethanol in 50 ml of dioxane, and the mixture was heated at 50° C. for 2 hours with stirring. The reaction solution was extracted with chloroform, washed with water and dried. The solvent was distilled off under reduced pressure. The residue was chromatographed on a silica gel column to afford 4.1 g (yield 41.7%) of 1,2-epoxy-3-[2-(2-hydroxyethoxy)phenoxy]-propane as a colorless oil.

A mixture of 2.9 g of acetic anhydride and 1.8 g of fuming nitric acid was added dropwise to a solution of 4.0 g of the resulting 1,2-epoxy-3-[2-(2-hydroxyethoxy)phenoxy]propane in 80 ml of acetonitrile at −30° C. to −10° C., and the mixture was stirred for 20 minutes. The same amount of the same mixture as above was further added, and the mixture was stirred for 20 minutes. After the reaction, the reaction mixture was extracted with chloroform, washed with water, and dried. The solvent was distilled off under reduced pressure. The residue was chromatographed on a silica gel column to afford 2.0 g (yield 41.2%) of 1,2-epoxy-3-[2-(2-nitratoethoxy)phenoxy]propane as colorless crystals having a melting point of 92° to 95° C.

20 ml of isopropylamine was added to a solution of 2.0 g of the resulting 1,2-epoxy-3-[2-(2-nitratoethoxy)phenoxy]propane in 150 ml of ethanol, and the mixture was stirred under reflux for 20 minutes. The reaction mixture was concentrated under reduced pressure. The residue was chromatographed on an alumina column to afford 2.4 g (yield 97.4%) of 1-isopropylamino-3-[2-(2-nitratoethoxy)-phenoxy]-2-propanol as colorless crystals having a melting point of 79° to 80° C.

Elemental analysis for $C_{14}H_{22}N_2O_6$:

| | C | H | N |
|---|---|---|---|
| Calculated (%): | 53.49 | 7.05 | 8.91 |
| Found (%): | 53.53 | 7.09 | 8.84 |

NMR spectrum ($\delta$, $CDCl_3$):

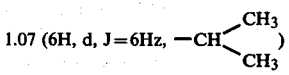

1.07 (6H, d, J=6Hz, —CH(CH$_3$)(CH$_3$))

4.40–4.16 (2H, m, —OCH$_2$CH$_2$ONO$_2$)
4.73–4.96 (2H, m, —OCH$_2$CH$_2$ONO$_2$)
6.97 (4H, s, H of the aromatic ring)
IR spectrum ($v_{max}^{KBr}$ cm$^{-1}$): 1630, 1280 (—NO$_2$).

EXAMPLE 3

1-iso-Propylamino-3-[[4-methoxy-3-(2-nitratoethoxy)]phenoxy]-2-propanol of the formula:

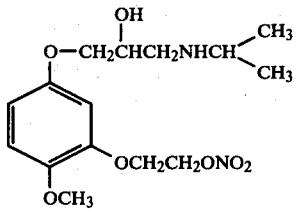

8.0 g of 2-[(5-ethoxycarbonyloxy-2-methoxy)phenoxy]ethanol was dissolved in 150 ml of anhydrous pyridine, and while cooling the solution with a chilling agent, 4.29 g of methanesulonyl chloride was added dropwise. The mixture was stirred for 1 hour. After the reaction, water was gradually added, and the mixture was extracted with chloroform. The chloroform layer was successively washed with 2 N hydrochloric acid, an aqueous solution of sodium hydrogen carbonate and an aqueous solution of sodium chloride, and dried. The solvent was distilled off to afford 10.32 g (yield 98.9%) of 2-[(5-ethoxycarbonyloxy-2-methoxy)phenoxy]ethylmesylate as colorless crystals.

9.79 g of the resulting 2-[(5-ethoxycarbonyloxy-2-methoxy)phenoxy]ethylmesylate and 16.7 g of sodium iodide were dissolved in 120 ml of dimethyl formamide, and the mixture was stirred at 120° C. for 2 hours. After the reaction, ethyl acetate was added. The extract was washed with an aqueous solution of sodium chloride, and the solvent was distilled off to afford 9.75 g of a crude product. The crude product was chromatographed on a silica gel column to afford 2.07 g (yield 19.3%) of 2-[(5-ethoxycarbonyloxy-2-methoxy)phenoxy]ethyliodide as pale yellow crystals.

1.97 g of the resulting 2-[(5-ethoxycarbonyloxy-2-methoxy)phenoxy]ethyliodide and 3.12 g of silver nitrate were dissolved in 20 ml of acetonitrile, and the solution was stirred at 70° C. for 45 minutes. After the reaction, the insoluble matter was removed by filtration. The mother liquor was concentrated, and the residue was extracted with ethyl acetate. The extract was washed with an aqueous solution of sodium chloride and dried. The solvent was distilled off to afford 1.62 g (yield 100%) of 2-[(5-ethoxycarbonyloxy-2-methoxy)-phenoxy]ethyl nitrate as pale yellow crystals. Then, 1.53 g of this product was dissolved in 12 ml of methanol, and 6.1 ml of 1 N sodium hydroxide was added. The mixture was stirred at room temperature for 30 minutes. After the reaction, 2 N hydrochloric acid was added to acidify it. Methanol was distilled off, and the residual aqueous solution was extracted with ethyl acetate. The extract was washed with an aqueous solution of sodium chloride. The extract was washed with an aqueous solution of sodium chloride, and dried. The solvent was distilled off to afford 1.08 g (yield 92.8%) of 2-[(5-hydroxy-2-methoxy)phenoxy]ethylnitrate as colorless acicular crystals.

1.06 g of the resulting 2-[(5-hydroxy-2-methoxy)-phenoxy]ethylnitrate was dissolved in 5.55 ml of 1 N sodium hydroxide, and 0.9 g of epichlorohydrin was added. The mixture was stirred at room temperature for 16 hours. After the reaction, the reaction mixture was extracted with chloroform. The extract was washed with an aqueous solution of sodium chloride and dried. The solvent was distilled off to afford 1.42 g of a crude product. The crude product was chromatographed on a silica gel column to afford 0.87 g (yield 65.9%) of 1,2-epoxy-3-[4-methoxh-3-(2-nitratoethoxy)phenoxy]propane.

0.52 g of the resulting 1,2-epoxy-3-[4-methoxy-3-(2-nitratoethoxy)phenoxy]propane and 4.9 ml of isopropylamine were dissolved in 40 ml of ethanol, and the solution was heated under reflux for 30 minutes. After the reaction, the reaction solution was concentrated, and the residue was chromatographed on a dilica gel column to afford 0.51 g (yield 81.2%) of 1-isopropylamino-3-[4-methoxy-3-(2-nitratoethoxy)phenoxy]-2-propanol as colorless prisms having a melting point of 93° to 94.5° C.

Elemental analysis for C₁₅H₂₄N₂O₇:

| | C | H | N |
|---|---|---|---|
| Calculated (%): | 52.32 | 7.03 | 8.14 |
| Found (%): | 52.40 | 7.13 | 8.05 |

NMR spectrum (δ, CDCl₃):

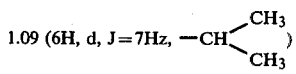

1.09 (6H, d, J=7Hz, —CH<CH₃/CH₃)

3.80 (2H, s, —OCH₃)
4.15–4.40 (2H, m, —OCH₂CH₂ONO₂)
4.70–4.93 (2H, m, —OCH₂CH₂ONO₂)
6.33–6.92 (3H, m, H of the aromatic ring)
IR spectrum ($v_{max}^{KBr}$ cm$^{-1}$): 1630, 1280 (—NO₂).

EXAMPLE 4

1-[4-methoxy-3-(2-nitratoethoxy)phenyl]-2-(1-methyl-3-phenylpropyl)aminoethanol of the formula:

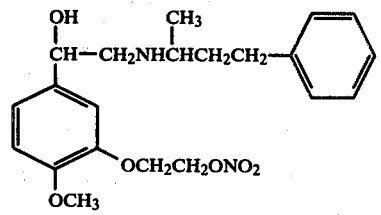

14.7 g of 4-methoxy-3-[2-(tetrahydro-2-pyranyloxy)ethoxy]styrene oxide was dissolved in 770 ml of ethanol, and 55 g of 4-phenyl-2-butylamine was added. The mixture was stirred at 90° C. for 40 minutes. After the reaction, the reaction mixture was concentrated under reduced pressure, and the residue was chromatographed on a silica gel column to afford 7.73 g (yield 34.9%) of 1-[4-methoxy-3-[2-(tetrahydro-2-pyranyloxy)ethoxy]phenyl]-2-(1-methyl-3-phenylpropyl)aminoethanol.

7.43 g of the resulting 1-[4-methoxy-3-[2-(tetrahydro-2-pyranyloxy-ethoxy]phenyl]aminoethanol was added to 400 ml of a mixture of acetic acid, water and acetone in a ratio of 9:2:2, and the mixture was stirred at 70° C. for 40 minutes. After the reaction, the reaction mixture was concentrated under reduced pressure, and the residue was chromatographed on a silica gel column to afford 5.46 g of a crude product. The crude product was dissolved in ethyl acetate, washed with 2 N sodium hydroxide and an aqueous solution of sodium chloride, and dried. The solvent was distilled off to afford 4.10 g (yield 68.1%) of 1-[3-(2-hydroxyethoxy)-4-methoxyphenyl]-2-(1-methyl-3-phenylpropyl)aminoethanol.

0.6 g of the resulting 1-[3-(2-hydroxyethoxy)-4-methoxyphenyl]-2-(1-methyl-3-phenylpropyl)aminoethanol was dissolved in 40 ml of acetonitrile, and while cooling the solution with a chilling agent, 0.4 ml of fuming nitric acid was added. Furthermore, a mixture of 1.1 g of acetic anhydride and 0.7 g of fuming nitric acid was added, and the mixture was stirred for 6 minutes. After the reaction, 6 ml of ethanol was added, and the mixture was stirred for 10 minutes. An excess of an aqueous solution of sodium hydrogen carbonate was added, and the mixture was extracted with ethyl acetate. The extract was washed with an aqueous solution of sodium chloride, and dried. The solvent was distilled off to afford 0.6 g of a yellow oil. When this oil was chromatographed on a silica gel column, 0.381 g (yield 56.4%) of 1-[4-methoxy-3-(2-nitratoethoxy)phenyl]-2-(1-methyl-3-phenylpropyl)aminoethanol was obtained as a pale yellow viscous oil.

Elemental analysis for C₂₁H₂₈N₂O₆:

| | C | H | N |
|---|---|---|---|
| Calculated (%): | 62.36 | 6.98 | 6.93 |
| Found (%): | 62.45 | 7.01 | 6.85 |

NMR spectrum (δ, CDCl₃/DC₃OD=4/1):

0.90–1.45 (3H, m, —CH₃)
3.80 (3H, s, —OCH₃)
4.10–4.40 (2H, m, —OCH₂CH₂ONO₂)
4.55–4.95 (2H, m, —OCH₂CH₂ONO₂)
6.65–7.35 (8H, m, H of the aromatic ring)

-continued

IR spectrum ($\nu_{max}^{liquid\,film}$ cm$^{-1}$): 1630, 1280 (—NO$_2$).

EXAMPLE 5

1-iso-Propylamino-3-(6-nitromethyl-2-pyridyloxy)-2-propanol of the formula:

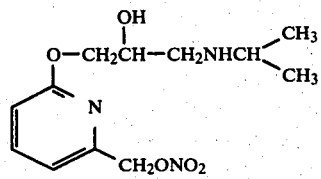

22.2 g of 2-phenyl-3-isopropyl-5-hydroxymethyloxazolidine was dissolved in 130 ml of anhydrous dimethyl formamide, and with stirring, 50% sodium hydride was added. To the resulting solution was added a solution of 22.75 g of 2-chloro-6-(tetrahydro-2-pyranyloxy)methylpyridine in 250 ml of anhydrous dimethyl formamide. The mixture was stirred at 80° C. for 1 hour. After the reaction, the solvent was distilled off under reduced pressure, and 500 ml of 10% hydrochloric acid was added. The mixture was stirred at 80° C. for 20 minutes. The reaction solution was evaporated to dryness under reduced pressure to afford 10 g (yield 41.6%) of 1-isopropylamino-3-(6-hydroxymethyl-2-pyridyloxy)-2-propanol.

5.3 g of the resulting 1-isopropylamino-3-(6-hydroxymethyl-2-pyridyloxy)-2-propanol was dissolved in 200 ml of acetonitrile. The solution was cooled to below 0° C., and 5.3 g of fuming nitric acid was added. The solution was stirred, and a mixture of 20.3 g of acetic anhydride and 11.2 g of fuming nitric acid was added. The mixture was then stirred for 10 minutes. After the reaction, the reaction solution was poured into an aqueous solution of sodium hydrogen carbonate, and stirred. The mixture was extracted with ethyl acetate. The extract was washed with an aqueous solution of sodium chloride, and dried. The ethyl acetate was distilled off to give 5.0 g of a crude product. When the crude product was chromatographed on a silica gel column, 2.0 g (yield 31.8%) of 1-isopropylamino-3-(6-nitratomethyl-2-pyridyloxy)-2-propanol was obtained as a pale yellow viscous oil.

Elemental analysis for C$_{12}$H$_{19}$N$_3$O$_5$:

|  | C | H | N |
|---|---|---|---|
| Calculated (%): | 50.52 | 6.71 | 14.73 |
| Found (%): | 50.60 | 6.73 | 14.65 |

NMR spectrum (δ, CDCl$_3$):

1.13 (6H, d, J = 6Hz, —CH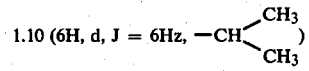)

4.43 (2H, d, J = 5Hz, —OCH$_2$CH(OH)—)
5.53 (2H, s, —CH$_2$ONO$_2$)
6.80–7.90 (3H, m, H of the aromatic ring)
IR spectrum ($\nu_{max}^{liquid\,film}$ cm$^{-1}$): 1630, 1280 (—NO$_2$).

In a similar manner, the compounds shown in the following Examples were obtained.

EXAMPLE 6

1-iso-Propylamino-3-[4-(2-nitratoethoxy)phenoxy]-2-propanol

Molecular formula: C$_{14}$H$_{22}$N$_2$O$_6$
Form: Colorless needles
Melting point: 63–64° C.
NMR spectrum (δ, CDCl$_3$):

1.10 (6H, d, J = 6Hz, —CH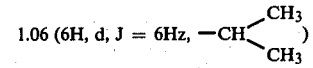)

4.27 (2H, t, J = 5Hz, —OCH$_2$CH$_2$ONO$_2$)
4.78 (2H, t, J = 5Hz, —OCH$_2$CH$_2$ONO$_2$)
6.85 (4H, S, H of the aromatic ring)
IR spectrum ($\nu_{max}^{KBr}$ cm$^{-1}$): 1630, 1280 (—NO$_2$)

1.0 g of 1-isopropylamino-3-[4-(2-nitratoethoxy)phenoxy]-2-propanol was dissolved in 20 ml of ethanol, and 0.8 ml of an HCl-ethanol solution (about 30% concentration) was added. The mixture was concentrated to dryness under reduced pressure. The resulting crystals were recrystallized twice from methanol-ether to obtain 0.58 g (76.2%) of the hydrochloride as colorless needles having a melting point of 110° to 112° C.

In a similar manner, the nitrate, sulfate, phosphate, oxalate, maleate, methanesulfonate, ethanesulfonate, p-toluenesulfonate, fumarate, malonate, and acetate of the above compound were prepared.

EXAMPLE 7

1-iso-Propylamino-3-[4-(3-nitratopropoxy)phenoxy]-2-propanol

Molecular formula: C$_{15}$H$_{24}$N$_2$O$_6$
Form: Colorless crystals
Melting point: 34–35° C.
NMR spectrum (δ, CDCl$_3$):

1.06 (6H, d, J = 6Hz, —CH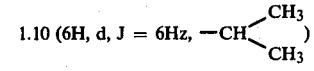)

2.16 (2H, quin, J = 6Hz, —CH$_2$CH$_2$CH$_2$ONO$_2$)
4.68 (2H, t, J = 6Hz, —CH$_2$CH$_2$CH$_2$ONO$_2$)
6.87 (4H, s, H of the aromatic ring)
IR spectrum ($\nu_{max}^{liquid\,film}$ cm$^{-1}$): 1630, 1280 (—NO$_2$)
Hydrochloride
Form: Colorless crystals
Melting point: 98–99° C.

EXAMPLE 8

1-iso-Propylamino-3-[2-(3-nitratopropoxy)phenoxy]-2-propanol

Molecular formula: C$_{15}$H$_{24}$N$_2$O$_6$
Form: Colorless needles
Melting point: 66° C.
NMR spectrum (δ, CDCl$_3$)

1.10 (6H, d, J = 6Hz, —CH$\left<\begin{array}{l}CH_3\\CH_3\end{array}\right.$)

4.13 (2H, t, J = 6Hz, —OCH$_2$CH$_2$CH$_2$ONO$_2$)
4.74 (2H, t, J = 6Hz, —OCH$_2$CH$_2$CH$_2$ONO$_2$)
6.95 (4H, s, H of the aromatic ring)
IR spectrum ($\nu_{max}^{KBr}$ cm$^{-1}$): 1625, 1280 (—NO$_2$)

EXAMPLE 9

1-t-butyl-Amino-3-[4-(2-nitratoethoxy)phenoxy]-2-propanol

Molecular formula: $C_{15}H_{24}N_2O_6$
Form: Pale yellow crystals
Melting point: 62–65° C.
NMR spectrum (δ, CDCl$_3$):
1.12 (9H, s, —C(CH$_3$)$_3$)
4.20 (2H, t, J = 5Hz, —OCH$_2$CH$_2$ONO$_2$)
4.83 (2H, t, J = 5Hz, —OCH$_2$CH$_2$ONO$_2$)
6.90 (4H, s, H of the aromatic ring)
IR spectrum ($\nu_{max}^{liquid\,film}$ cm$^{-1}$): 1620, 1280 (—NO$_2$)

EXAMPLE 10

1-t-butyl-Amino-3-[3-(2-nitratoethoxy)phenoxy]-2-propanol

Molecular formula: $C_{15}H_{24}N_2O_6$
Form: Colorless needles
Melting point: 84–86° C.
NMR spectrum (δ, CDCl$_3$)
1.13 (9H, s, —C(CH$_3$)$_3$)
4.13–4.33 (2H, m, —OCH$_2$CH$_2$ONO$_2$)
4.70–4.93 (2H, m, —OCH$_2$CH$_2$ONO$_2$)
6.40–6.70 (3H, m, H of the aromatic ring)
7.00–7.40 (1H, m, H of the aromatic ring)
IR spectrum ($\nu_{max}^{KBR}$ cm$^{-1}$): 1630, 1280 (—NO$_2$)

EXAMPLE 11

1-(1-Ethylpropyl)amino-3-[4-(2-nitratoethoxy)phenoxy]-2-propanol

Molecular formula: $C_{16}H_{26}N_2O_6$
Form: Pale yellow viscous oil
NMR spectrum (δ, CDCl$_3$):

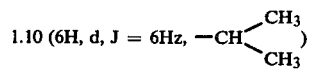
0.90 (6H, t, J = 6Hz, —CH(CH$_2$CH$_3$)$_2$)

4.20 (2H, t, J = 5Hz, —OCH$_2$CH$_2$ONO$_2$)
4.80 (2H, t, J = 5Hz, —OCH$_2$CH$_2$ONO$_2$)
6.86 (4H, s, H of the aromatic ring)
IR spectrum ($\nu_{max}^{liquid\,film}$ cm$^{-1}$): 1620, 1280 (—NO$_2$)

EXAMPLE 12

1-iso-Propylamino-3-[3-(3-nitratopropoxy)phenoxy]-2-propanol

Molecular formula: $C_{15}H_{24}N_2O_6$
Form: Colorless needles
Melting point: 63–65.5° C.
NMR spectrum (δ, CDCl$_3$):

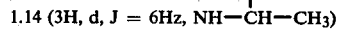
1.07 (6H, d, J = 6Hz, —CH(CH$_3$)$_2$)

2.10 (2H, quin, J = 6Hz, —OCH$_2$CH$_2$CH$_2$ONO$_2$)
4.63 (2H, t, J = 6Hz, —OCH$_2$CH$_2$CH$_2$ONO$_2$)
6.30–6.63 (3H, m, H of the aromatic ring)
6.96–7.33 (1H, m, H of the aromatic ring)
IR spectrum ($\nu_{max}^{liquid\,film}$ cm$^{-1}$): 1630, 1280 (—NO$_2$)

EXAMPLE 13

1-iso-Propylamino-3-[2-methoxy-5-(2-nitratoethoxy)phenoxy]-2-propanol

Molecular formula: $C_{15}H_{24}N_2O_7$
Form: Pale yellow viscous oil
NMR spectrum (δ, CDCl$_3$):

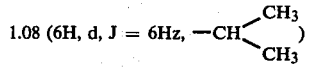
1.10 (6H, d, J = 6Hz, —CH(CH$_3$)$_2$)

3.80 (3H, s, —OCH$_3$)
4.15 (2H, t, J = 5Hz, —OCH$_2$CH$_2$ONO$_2$)
4.76 (2H, t, J = 5Hz, —OCH$_2$CH$_2$ONO$_2$)
6.30–6.90 (3H, m, H of the aromatic ring)
IR spectrum ($\nu_{max}^{liquid\,film}$ cm$^{-1}$): 1630, 1290 (—NO$_2$)

EXAMPLE 14

1-[2-(2-Nitratoethoxy)phenyl]-2-(1-methyl-3-phenylpropyl)aminoethanol

Molecular formula: $C_{20}H_{26}N_2O_5$
Form: Pale yellow viscous oil
NMR spectrum (δ, CDCl$_3$)

1.14 (3H, d, J = 6Hz, NH—CH(—CH$_3$))

4.20 (2H, t, J = 5Hz, —OCH$_2$CH$_2$ONO$_2$)
4.77 (2H, t, J = 5Hz, —OCH$_2$CH$_2$ONO$_2$)
6.65–7.60 (9H, m, H of the aromatic ring)
IR spectrum ($\nu_{max}^{liquid\,film}$ cm$^{-1}$): 1620, 1280 (—NO$_2$)

EXAMPLE 15

1-iso-Propylamino-3-[6-(2-nitratoethoxy)-2-pyridyloxy]-2-propanol

Molecular formula: $C_{13}H_{21}N_3O_6$
Form: Colorless viscous oil
NMR spectrum (δ, CDCl$_3$):

1.08 (6H, d, J = 6Hz, —CH(CH$_3$)$_2$)

4.43–4.65 (2H, m, —OCH$_2$CH$_2$ONO$_2$)
4.67–4.90 (2H, m, —OCH$_2$CH$_2$ONO$_2$)
6.34 (1H, d, J = 8Hz, H of the aromatic ring)
6.37 (1H, d, J = 8Hz, H of the aromatic ring)
7.53 (1H, t, J = 8Hz, H of the aromatic ring)
IR spectrum ($\nu_{max}^{liquid\,film}$ cm$^{-1}$): 1620, 1280 (—NO$_2$)

EXAMPLE 16

1-iso-Propylamino-3-[5-nitratomethyl-2-pyridyloxy]-2-propanol

Molecular formula: $C_{12}H_{19}N_3O_5$
Form: Pale yellow viscous oil
NMR spectrum (δ, CDCl$_3$):

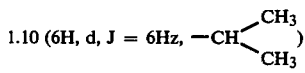
1.10 (6H, d, J = 6Hz, —CH(CH$_3$)$_2$)

4.36 (2H, d, J = 5Hz, —OCH$_2$—CH(—OH)—)

5.35 (2H, s, —CH$_2$ONO$_2$)
6.75 (1H, d, J = 9Hz, H$_A$)
7.70 (1H, dd, J = 9Hz, 2Hz, H$_B$)
8.18 (1H, d, J = 2Hz, H$_C$)

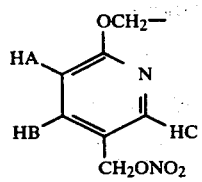

IR spectrum ($\nu_{max}^{liquid\ film}$ cm$^{-1}$): 1620, 1280 (—NO$_2$)

EXAMPLE 17

1-iso-Propylamino-3-[2-methoxy-4-(2-nitratoethoxy)-phenoxy]-2-propanol

Molecular formula: C$_{15}$H$_{24}$N$_2$O$_7$
Form: Pale yellow crystals
Melting point: 66–69° C.
NMR spectrum (δ, CDCl$_3$):

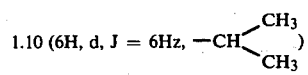

3.80 (3H, s, —OCH$_3$)
4.16 (2H, t, J = 5Hz, —OCH$_2$CH$_2$ONO$_2$)
4.80 (2H, t, J = 5Hz, —OCH$_2$CH$_2$ONO$_2$)
6.20–6.95 (3H, m, H of the aromatic ring)
IR spectrum ($\nu_{max}^{liquid\ film}$ cm$^{-1}$): 1620, 1280 (—NO$_2$)

EXAMPLE 18

1-iso-Propylamino-3-[4-methyl-3-(2-nitratoethoxy)-phenoxy]-2-propanol

Molecular formula: C$_{15}$H$_{24}$N$_2$O$_6$
Form: Colorless crystals
Melting point: 45–52° C.
NMR spectrum (δ, CDCl$_3$):

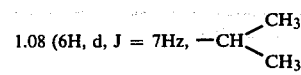

2.12 (3H, s, 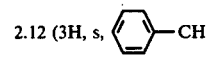—CH$_3$)

4.07–4.28 (2H, m, —OCH$_2$CH$_2$ONO$_2$)
4.70–4.93 (2H, m, —OCH$_2$CH$_2$ONO$_2$)
6.27–6.53 (2H, m, H$_A$)
6.99 (1H, d, H$_B$)

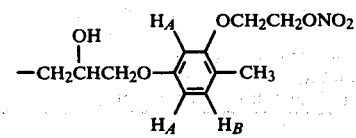

IR spectrum ($\nu_{max}^{KBr}$ cm$^{-1}$): 1620, 1280 (—NO$_2$)

EXAMPLE 19

1-t-butyl-Amino-3-[4-(3-nitratopropoxy)phenoxy]-2-propanol

Molecular formula: C$_{16}$H$_{26}$N$_2$O$_6$
Form: Pale yellow viscous oil
NMR spectrum (δ, CDCl$_3$):
1.1 (9H, s, —C(CH$_3$)$_3$)
4.65 (2H, t, J = 6Hz, —CH$_2$ONO$_2$)
6.8 (4H, s, H of the aromatic ring)
IR spectrum ($\nu_{max}^{liquid\ film}$ cm$^{-1}$): 1640, 1280 (—NO$_2$)

EXAMPLE 20

1-(1-Ethylpropyl)amino-3-[4-(3-nitratopropoxy)-phenoxy]-2-propanol

Molecular formula: C$_{17}$H$_{28}$N$_2$O$_6$
Form: Colorless viscous oil
NMR spectrum (δ, CDCl$_3$):

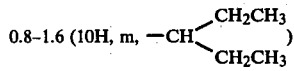

4.6 (2H, t, J = 6Hz, —CH$_2$ONO$_2$)
6.8 (4H, s, H of the aromatic ring)
IR spectrum ($\nu_{max}^{liquid\ film}$ cm$^{-1}$): 1630, 1280 (—NO$_2$)

EXAMPLE 21

1-iso-Propylamino-3-[2-acetyl-4-(2-nitratoethoxy)-phenoxy]-2-propanol

Molecular formula: C$_{16}$H$_{24}$N$_2$O$_7$
Form: Pale yellow prisms
Melting point: 76–78° C.
NMR spectrum (δ, CDCl$_3$):

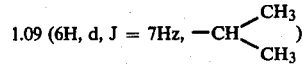

2.62 (3H, s, —COCH$_3$)
4.10–4.30 (2H, m, —OCH$_2$CH$_2$ONO$_2$)
4.63–4.87 (2H, m, —OCH$_2$CH$_2$ONO$_2$)
6.87–7.00 (2H, m, H$_A$)
7.12–7.27 (1H m, H$_B$)

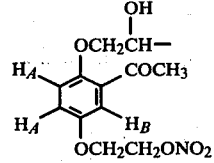

IR spectrum ($\nu_{max}^{KBr}$ cm$^{-1}$):
1660 (COCH$_3$), 1620, 1280 (—NO$_2$)

EXAMPLE 22

1-iso-Propylamino-3-[4-(2-methyl-2-nitratoethoxy)-phenoxy]-2-propanol

Molecular formula: C$_{15}$H$_{24}$N$_2$O$_6$
Form: Colorless viscous oil
NMR spectrum (δ, CDCl$_3$):

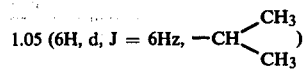

1.43 (3H, d, J = 6Hz, —CHCH$_3$)

-continued

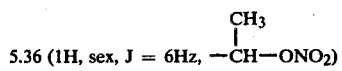
5.36 (1H, sex, J = 6Hz, —CH—ONO₂)

6.76 (4H, s, H of the aromatic ring)
IR spectrum ($\nu_{max}^{liquid\,film}$ cm⁻¹): 1630, 1282 (—NO₂)

EXAMPLE 23

1-iso-Propylamino-3-[2-allyloxy-4-(2-nitratoethoxy)-phenoxy]-2-propanol

Molecular formula: $C_{17}H_{26}N_2O_7$
Form: Pale yellow crystals
Melting point: 54–57° C.
NMR spectrum (δ, CDCl₃):

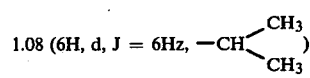
1.08 (6H, d, J = 6Hz, —CH(CH₃)₂)

4.16 (2H, t, J = 5Hz, —OCH₂CH₂ONO₂)
4.80 (2H, t, J = 5Hz, —OCH₂CH₂ONO₂)
4.53 (2H, d, J = 5Hz, —OCH₂CH=CH₂)
5.16–5.60 (2H, m, —OCH₂CH=CH₂)
5.80–6.20 (1H, m, —OCH₂CH=CH₂)
6.20–7.00 (3H, m, H of the aromatic ring)
IR spectrum ($\nu_{max}^{liquid\,film}$ cm⁻¹): 1630, 1280 (—NO₂)

EXAMPLE 24

1-t-butylamino-3-[2-(2-nitratoethoxy)phenoxy]-2-propanol

Molecular formula: $C_{15}H_{24}N_2O_6$
Form: Colorless viscous oil
NMR spectrum (δ, CDCl₃):
1.1 (9H, s, —C(CH₃)₃)
3.8–4.9 (7H, m, —OCH₂CH₂ONO₂,

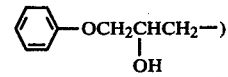
—OCH₂CHCH₂—)
       |
       OH 6.9 (4H, s, H of the aromatic ring)
IR spectrum ($\nu_{max}^{liquid\,film}$ cm⁻¹): 1630, 1280 (—NO₂)

EXAMPLE 25

1-(1-Ethylpropyl)amino-3-[2-(2-nitratoethoxy)-phenoxy]-2-propanol

Molecular formula: $C_{16}H_{26}N_2O_6$
Form: Colorless viscous oil
NMR spectrum (δ, CDCl₃)

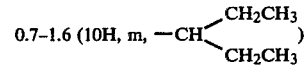
0.7–1.6 (10H, m, —CH(CH₂CH₃)₂)

4.16–4.40 (2H, m, —OCH₂CH₂ONO₂)
4.70–4.95 (2H, m, —OCH₂CH₂ONO₂)
6.90 (4H, s, H of the aromatic ring)
IR spectrum ($\nu_{max}^{liquid\,film}$ cm⁻¹): 1610, 1280 (—NO₂)

EXAMPLE 26

1-(1-Ethylpropyl)amino-3-[3-(3-nitratopropoxy)-phenoxy]-2-propanol

Molecular formula: $C_{17}H_{28}N_2O_6$
Form: Colorless viscous oil
NMR spectrum (δ, CDCl₃):

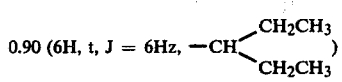
0.90 (6H, t, J = 6Hz, —CH(CH₂CH₃)₂)

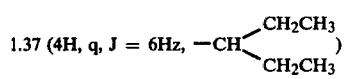
1.37 (4H, q, J = 6Hz, —CH(CH₂CH₃)₂)

4.06 (2H, t, J = 6Hz, —OCH₂CH₂CH₂ONO₂)
4.66 (2H, t, J = 6Hz, —OCH₂CH₂CH₂ONO₂)
6.33–6.66 (3H, m, H of the aromatic ring)
7.00–7.40 (1H, m, H of the aromatic ring)
IR spectrum ($\nu_{max}^{liquid\,film}$ cm⁻¹): 1630, 1280 (—NO₂)

EXAMPLE 27

1-(1-Phenyl)benzylamino-3-[4-(3-nitratopropoxy)-phenoxy]-2-propanol

Molecular formula: $C_{25}H_{28}N_2O_6$
Form: Pale yellow viscous oil
NMR spectrum (δ, CDCl₃):

OH
                            |
3.80–4.20 (5H, m.—OCH₂CH—,

—OCH₂CH₂CH₂ONO₂)
4.63 (2H, t, J = 6Hz, —OCH₂CH₂CH₂ONO₂)

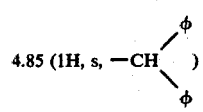
4.85 (1H, s, —CH(φ)₂)

6.80 (4H, s, H of the aromatic ring)
7.10–7.50 (10H, m, H of the aromatic ring)
IR spectrum ($\nu_{max}^{liquid\,film}$ cm⁻¹): 1625, 1280 (—NO₂)

EXAMPLE 28

1-(1-Propyl)butylamino-3-[4-(2-nitratoethoxy)-phenoxy]-2-propanol

Molecular formula: $C_{18}H_{30}N_2O_6$
Form: Colorless crystals
Melting point: 56–57° C.
NMR spectrum (δ, CDCl₃):

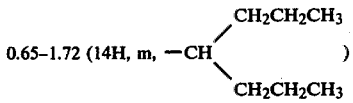
0.65–1.72 (14H, m, —CH(CH₂CH₂CH₃)₂)

3.72–4.40 (5H, m, —OCH₂CHOH, —OCH₂CH₂ONO₂)

4.60–4.90 (2H m, —OCH₂CH₂ONO₂)
6.80 (4H, s, H of the aromatic ring)
IR spectrum ($\nu_{max}^{KBr}$ cm⁻¹): 1630,1280 (—NO₂)

EXAMPLE 29

1-(1-Ethyl)propylamino-3-[3-(2-nitratoethoxy)-phenoxy]-2-propanol

Molecular formula: $C_{16}H_{26}N_2O_6$

-continued

Form: Pale yellow viscous oil
NMR spectrum (δ, CDCl₃):

0.70–1.06 (6H, m, 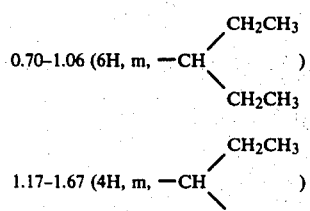)

1.17–1.67 (4H, m, —CH(CH₂CH₃)(CH₂CH₃))

4.13–4.33 (2H, m, —OCH₂CH₂ONO₂)
4.70–4.92 (2H, m, —OCH₂CH₂ONO₂)
6.33–6.70 (3H, m, H of the aromatic ring)
7.03–7.40 (1H, m, H of the aromatic ring)
IR spectrum ($\nu_{max}^{liquid\,film}$ cm⁻¹): 1630, 1280 (—NO₂)

EXAMPLE 30

1-(1-Propyl)butylamino-3-[3-(2-nitratoethoxy)-phenoxy]-2-propanol

Molecular formula: $C_{18}H_{30}N_2O_6$
Form: Colorless viscous oil
NMR spectrum (δ, CDCl₃):

0.65–1.66 (14H, m, —CH(CH₂CH₂CH₃)(CH₂CH₂CH₃))

3.77–4.20 (5H, m, —OCH₂CH(OH)—, —OCH₂CH₂ONO₂)
4.67–4.96 (2H, m, —OCH₂CH₂ONO₂)
6.38–6.72 (3H, m, H of the aromatic ring)
7.00–7.40 (1H, m, H of the aromatic ring)
IR spectrum ($\nu_{max}^{liquid\,film}$ cm⁻¹): 1630, 1280 (—NO₂)

EXAMPLE 31

1-(1-Phenyl)benzylamino-3-[3-(2-nitratoethoxy)-phenoxy]-2-propanol

Molecular formula: $C_{24}H_{26}N_2O_6$
Form: Colorless viscous oil
NMR spectrum (δ, CCl₄):
2.52–2.85 (2H, m, —CH₂NO—)
3.73–4.22 (5H, m, —OCH₂CH(OH)—, —OCH₂CH₂ONO₂)

4.52–4.82 (3H, m, —OCH₂CH₂ONO, —CH(φ)(φ))

6.25–6.56 (3H, m, H of the aromatic ring)
6.90–7.50 (11H, m, H of the aromatic ring)
IR spectrum ($\nu_{max}^{liquid\,film}$ cm⁻¹): 1630, 1275 (—NO₂)

EXAMPLE 32

1-iso-Propylamino-3-[2-(6-nitratohexyloxy)phenoxy]-2-propanol

Molecular formula: $C_{18}H_{30}N_2O_6$
Form: Colorless crystals
Melting point: 51–53° C.
NMR spectrum (δ, CDCl₃):

1.07 (6H, d, J=6Hz, —CH(CH₃)(CH₃))

4.00 (2H, t, J=6Hz, —OCH₂CH₂—)
4.45 (2H, t, J=6Hz, —CH₂ONO₂)
6.90 (4H, s, H of the aromatic ring)
IR spectrum ($\nu_{max}^{KBr}$ cm⁻¹): 1630, 1290 (—NO₂)

EXAMPLE 33

1-iso-Propylamino-3-[2-allyloxy-5-chloro-4-(2-nitratoethoxy)phenoxy]-2-propanol

Molecular formula: $C_{17}H_{25}N_2O_7Cl$
Form: Pale yellow crystals
Melting point: 75–76° C.
NMR spectrum (δ, CDCl₃):

1.08 (6H, d, J=6Hz, —CH(CH₃)(CH₃))

4.20 (2H, t, J=5Hz, —OCH₂CH₂ONO₂)
4.80 (2H, t, J=5Hz, —OCH₂CH₂ONO₂)
4.52 (2H, d, J=5Hz, —OCH₂CH=CH₂)
5.15–5.60 (2H, m, —OCH₂CH=CH₂)
5.85–6.40 (1H, m, —OCH₂CH=CH₂)

6.57 (1H, s, H$_A$)
6.93 (1H, s, H$_B$)

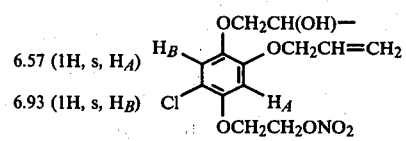

IR spectrum ($\nu_{max}^{KBr}$ cm⁻¹): 1620, 1280 (—NO₂)

EXAMPLE 34

1-iso-Propylamino-3-[3-chloro-4-(2-nitratoethoxy)-phenoxy]-2-propanol

Molecular formula: $C_{14}H_{21}N_2O_6Cl$
Form: Pale yellow crystals
Melting point: 46–47° C.
NMR spectrum (δ, CDCl₃):

1.11 (6H, d, J=7Hz, —CH(CH₃)(CH₃))

4.13–4.38 (2H, m, —OCH₂CH₂ONO₂)
4.73–4.97 (2H, m, —OCH₂CH₂ONO₂)
6.77–7.08 (3H, m, H of the aromatic ring)
IR spectrum ($\nu_{max}^{KBr}$ cm⁻¹): 1620, 1280 (—NO₂)

EXAMPLE 35

1-iso-Propylamino-3-[(3-nitratomethyl)phenoxy]-2-propanol

Molecular formula: $C_{13}H_{20}N_2O_5$
Form: Pale yellow viscous oil
NMR spectrum (δ, CDCl₃):

1.12 (6H, d, J=6Hz, —CH(CH₃)(CH₃))

3.80–4.15 (3H, m, —OCH₂CH(OH)—)
5.43 (2H, s, —CH₂ONO₂)
6.80–7.40 (4H, m, H of the aromatic ring)
IR spectrum ($\nu_{max}^{liquid\,film}$ cm⁻¹): 1620, 1280 (—NO₂)

EXAMPLE 36

1-(1-Phenyl)benzylamino-3-[4-(2-nitratoethoxy)-phenoxy]-2-propanol

Molecular formula: $C_{24}H_{26}N_2O_6$
Form: Colorless viscous oil
NMR spectrum (δ, $CDCl_3$):
  3.80–4.25 (5H, m, $-OCH_2CH(OH)-$, $-OCH_2CH_2ONO_2$)
  4.60–4.85 (3H, m, $-CH_2ONO_2$, $-CH(\phi)(\phi)$)
  6.80 (4H, s, H of the aromatic ring)
  7.10–7.45 (10H, m, H of the aromatic ring)
  IR spectrum ($\nu_{max}^{liquid\ film}$ cm$^{-1}$): 1625, 1280 ($-NO_2$)

EXAMPLE 37

1-[3-(2,4-Dimethylpentyl)amino]-3-[4-(2-nitratoethoxy)phenoxy]-2-propanol

Molecular formula: $C_{18}H_{30}N_2O_6$
Form: Colorless viscous oil
NMR spectrum (δ, $CCl_4$):

0.66–1.13 (12H, m, $(-CH(CH_3)(CH_3))_2$)

4.00–4.23 (2H, m, $-OCH_2CH_2ONO_2$)
  4.57–4.82 (2H, m, $-OCH_2CH_2ONO_2$)
  6.75 (4H, s, H of the aromatic ring)
  IR spectrum ($\nu_{max}^{liquid\ film}$ cm$^{-1}$): 1630, 1280 ($-NO_2$)

EXAMPLE 38

1-[(1,1-Diethyl)propylamino]-3-[4-(2-nitratoethoxy)-phenoxy]-2-propanol

Molecular formula: $C_{18}H_{30}N_2O_6$
Form: Colorless crystals
Melting point: 56–57° C.
NMR spectrum (δ, $CDCl_3$):
  0.48–1.04 (9H, m, $-C(CH_2CH_3)_3$)
  1.04–1.55 (6H, m, $-C(CH_2CH_3)_3$)
  3.75–4.33 (5H, m, $-OCH_2CH(OH)-$, $-OCH_2CH_2ONO_2$)
  4.68–4.93 (2H, m, $-OCH_2CH_2ONO_2$)
  6.86 (4H, s, H of the aromatic ring)
  IR spectrum ($\nu_{max}^{KBr}$ cm$^{-1}$): 1630, 1280 ($-NO_2$)

EXAMPLE 39

1-(1-Propyl)butylamino-3-[4-(3-nitratopropoxy)-phenoxy]-2-propanol

Molecular formula: $C_{19}H_{32}N_2O_6$
Form: Colorless viscous oil
NMR spectrum (δ, $CDCl_3$):

0.60–1.70 (14H, m, $-CH(CH_2CH_2CH_3)(CH_2CH_2CH_3)$)

3.70–4.20 (5H, m, $-OCH_2CH(OH)-$, $-OCH_2CH_2CH_2ONO_2$)
  4.65 (2H, t, J=6Hz, $-OCH_2CH_2CH_2ONO_2$)
  6.80 (4H, s, H of the aromatic ring)
  IR spectrum ($\nu_{max}^{liquid\ film}$ cm$^{-1}$): 1620, 1280 ($-NO_2$)

EXAMPLE 40

1-[(1,1-Diethyl)propylamino]-3-[4-(3-nitratopropoxy)phenoxy]-2-propanol

Molecular formula: $C_{19}H_{32}N_2O_6$
Form: Colorless viscous oil
NMR spectrum (δ, $CDCl_3$):
  0.54–1.02 (9H, m, $-C(CH_2CH_3)_3$)
  1.02–1.53 (6H, m, $-C(CH_2CH_3)_3$)
  3.80–4.17 (5H, m, $-OCH_2CH(OH)-$, $-OCH_2CH_2CH_2ONO_2$)
  4.66 (2H, t, J = 6Hz, $-OCH_2CH_2CH_2ONO_2$)
  6.83 (4H, s, H of the aromatic ring)
  IR spectrum ($\nu_{max}^{liquid\ film}$ cm$^{-1}$): 1640, 1280 ($-NO_2$)

EXAMPLE 41

1-(1-Phenyl)benzylamino-3-[2-(2-nitratoethoxy)-phenoxy]-2-propanol

Molecular formula: $C_{24}H_{26}N_2O_6$
Form: Colorless viscous oil
NMR spectrum (δ, $CDCl_3$):
  4.0–4.5 (5H, m, $-OCH_2CH(OH)-$, $-OCH_2CH_2ONO_2$)
  4.68 (2H, t, J=5Hz, $-OCH_2CH_2ONO_2$)
  4.90 (1H, s, $-CH(\phi)(\phi)$)
  6.90 (4H, s, H of the aromatic ring)
  7.10–7.50 (10H, m, H of the aromatic ring)
  IR spectrum ($\nu_{max}^{liquid\ film}$ cm$^{-1}$): 1630, 1280 ($-NO_2$)

EXAMPLE 42

1-[3-(2,4-Dimethylpentyl)amino]-3-[2-(2-nitratoethoxy)phenoxy]-2-propanol

Molecular formula: $C_{18}H_{30}N_2O_6$
Form: Pale yellow viscous oil
NMR spectrum (δ, $CCl_4$)

0.68–1.10 (12H, m, $(-CH(CH_3)(CH_3))_2$)

1.50–2.02 (3H, m, $-CH(CH)(CH)$)

4.10–4.32 (2H, m, $-OCH_2CH_2ONO_2$)
  4.60–4.87 (2H, m, $-OCH_2CH_2ONO_2$)
  6.84 (4H, s, H of the aromatic ring)
  IR spectrum ($\nu_{max}^{liquid\ film}$ cm$^{-1}$): 1630, 1280 ($-NO_2$)

EXAMPLE 43

1-[(1,1-Diethyl)propylamino]-3-[2-(2-nitratoethoxy)-phenoxy]-2-propanol

Molecular formula: $C_{18}H_{30}N_2O_6$
Form: Colorless viscous oil
NMR specturm (δ, $CDCl_3$)
  0.5–1.6 (15H, m, $-C(CH_2CH_3)_3$)
  3.80–4.15 (3H, m, $-OCH_2CH(OH)-$)
  4.15–4.35 (2H, m, $-OCH_2CH_2ONO_2$)

4.70–4.85 (2H, m, —OCH₂CH₂ONO₂)
6.90 (4H, s, H of the aromatic ring)

IR spectrum ($\nu_{max}^{liquid\,film}$ cm⁻¹): 1640, 1280 (—NO₂)

EXAMPLE 44

1-[3-(2,4-Dimethylpentyl)amino]-3-[3-(2-nitratoethoxy)phenoxy]-2-propanol

Molecular formula: $C_{18}H_{30}N_2O_6$
Form: Colorless viscous oil
NMR spectrum (δ, CCl₄):

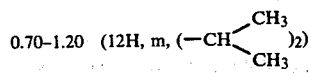
0.70–1.20 (12H, m, (—CH(CH₃)₂)₂)

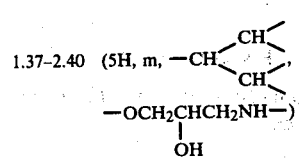
1.37–2.40 (5H, m, —CH(CH<)(CH<), —OCH₂CHCH₂NH—)
                                              |
                                              OH 3.76–4.10 (3H, s, —OCH₂CH(OH)—)
4.05–4.30 (2H, m, —OCH₂CH₂ONO₂)
4.60–4.90 (2H, m, —OCH₂H₂ONO₂)
6.30–6.66 (3H, m, H of the aromatic ring)
6.96–7.33 (1H, m, H of the aromatic ring)

IR spectrum ($\nu_{max}^{liquid\,film}$ cm⁻¹): 1630, 1280 (—NO₂)

EXAMPLE 45

1-[(1,1-Diethyl)propylamino]-3-[3-(2-nitratoethoxy)phenoxy]-2-propanol

Molecular formula: $C_{18}H_{30}N_2O_6$
Form: Colorless viscous oil
0.57–1.07 (9H, m, —C(CH₂CH₃)₃)
1.07–1.65 (6H, m, —C(CH₂CH₃)₃)
3.70–4.45 (5H, m, —OCH₂CH(OH)—, —OCH₂CH₂ONO₂)
4.60–4.95 (2H, m, —OCH₂CH₂ONO₂)
6.38–6.80 (3H, m, H of the aromatic ring)
7.00–7.42 (1H, m, H of the aromatic ring)

IR spectrum ($\nu_{max}^{liquid\,film}$ cm⁻¹): 1630, 1280 (—NO₂)

EXAMPLE 46

1-[3-(2,4-Dimethylpentyl)amino]-3-[4-(3-nitratopropoxy)phenoxy]-2-propanol

Molecular formula: $C_{19}H_{32}N_2O_6$
Form: Colorless viscous oil
NMR spectrum (δ, CDCl₃):

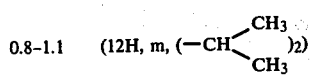
0.8–1.1 (12H, m, (—CH(CH₃)₂)₂)

3.80–4.20 (5H, m, —OCH₂CH(OH)—, —OCH₂CH₂ONO₂)
4.68 (2H, t, J=6Hz, —OCH₂CH₂ONO₂)
6.85 (4H, s, H of the aromatic ring)

IR spectrum ($\nu_{max}^{liquid\,film}$ cm⁻¹): 1630, 1280 (—NO₂)

EXAMPLE 47

1-[(1-propyl)butylamino]-3-[2-(2-nitratoethoxy)phenoxy]-2-propanol

Molecular formula: $C_{18}H_{30}N_2O_6$
Form: Colorless viscous oil
NMR spectrum (δ, CDCl₃):

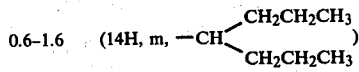
0.6–1.6 (14H, m, —CH(CH₂CH₂CH₃)(CH₂CH₂CH₃))

4.15–4.40 (2H, m, —OCH₂CH₂ONO₂)
4.60–4.92 (2H, m, —OCH₂CH₂ONO₂)
6.90 (4H, s, H of the aromatic ring)

IR spectrum ($\nu_{max}^{liquid\,film}$ cm⁻¹): 1620, 1280 (—NO₂)

EXAMPLE 48 bis-[[2-hydroxy-3-(4-nitratoethoxy)phenoxy]propyl]-(1-propyl)butylamine

Molecular formula: $C_{29}H_{43}N_3O_{12}$
Form: Colorless viscous oil
NMR spectrum (δ, CDCl₃):

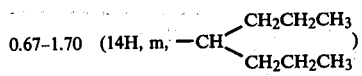
0.67–1.70 (14H, m, —CH(CH₂CH₂CH₃)(CH₂CH₂CH₃))

2.27–2.90 (4H, m, (—CH₂)₂N—)
3.35 (2H, s, —OH)
3.75–4.35 (10H, m, —OCH₂CH(OH)—, —OCH₂CH₂ONO₂)
4.67–4.93 (4H, m, —OCH₂CH₂ONO₂)
6.83 (8H, s, H of the aromatic ring)

IR spectrum ($\nu_{max}^{liquid\,film}$ cm⁻¹): 1630, 1280 (—NO₂)

EXAMPLE 49

1-iso-Propylamino-3-[4-(2-nitratoethyl)phenoxy]-2-propanol

Molecular formula: $C_{14}H_{22}N_2O_5$
Form: Colorless crystals
Melting point: 74–74.5° C.
NMR spectrum (δ, CDCl₃):

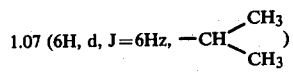
1.07 (6H, d, J=6Hz, —CH(CH₃)₂)

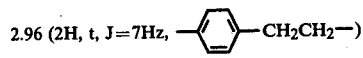
2.96 (2H, t, J=7Hz, —⟨⟩—CH₂CH₂—)

4.62 (2H, t, J=7Hz, —OCH₂ONO₂)
6.90 (2H, d, J=9Hz, H of the aromatic ring)
7.18 (2H, d, J=9Hz, H of the aromatic ring)

IR spectrum ($\nu_{max}^{KBr}$ cm⁻¹): 1640, 1280 (—NO₂)

EXAMPLE 50

1-iso-Propylamino-3-[2,4-di-(2-nitratoethoxy)phenoxy]-2-propanol

Molecular formula: $C_{16}H_{25}N_3O_{10}$
Form: Colorless crystals
Melting point: 70–73° C.

-continued

NMR spectrum (δ, CDCl₃):

1.10 (6H, d, J=6Hz, 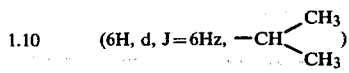)

4.10-4.40 (4H, m, (—OCH₂CH₂ONO₂)₂)
4.55-5.00 (4H, m, (—OCH₂CH₂ONO₂)₂)
6.47 (1H d.d, J=8Hz, 2Hz, H$_B$)
6.53 (1H, s, H$_C$)
6.90 (1H, d.d, J=8Hz, 1Hz, H$_A$)

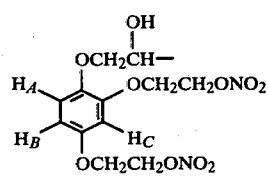

IR spectrum ($\nu_{max}^{KBr}$ cm⁻¹): 1630, 1280 (—NO₂)

EXAMPLE 51

1-iso-Propylamino-3-[2-hydroxy-4-(2-nitratoethoxy)-phenoxy]-2-propanol

Molecular formula: C₁₄H₂₂N₂O₇
Form: Colorless viscous oil
NMR spectrum: (δ, CDCl₃):

1.04 (6H, d, —CH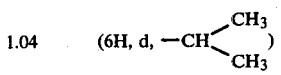)

3.63-4.27 (5H, m, —OCH₂CH(OH)—, —OCH₂CH₂ONO₂)
4.57-4.83 (2H, m, —OCH₂CH₂ONO₂)
5.43 (3H, s, (—OH)₂, —NH—)
6.07-6.83 (3H, m, H of the aromatic ring)

IR spectrum ($\nu_{max}^{liquid\ film}$ cm⁻¹): 1630, 1280 (—NO₂)

EXAMPLE 52

1-iso-Propylamino-3-[4-(6-nitratohexyloxy)phenoxy]-2-propanol

Molecular formula: C₁₈H₃₀N₂O₆
Form: Colorless crystals
Melting point: 50-52.5° C.
NMR spectrum (δ, CDCl₃):

1.07 (6H, d, J=6Hz, —CH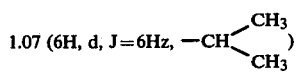)

4.48 (2H, t, J=7Hz, —CH₂ONO₂)
6.86 (4H, s, H of the aromatic ring)

IR spectrum ($\nu_{max}^{KBr}$ cm⁻¹): 1630, 1280 (—NO₂)

EXAMPLE 53

1-iso-Propylamino-3-[3-(2-nitratoethoxy)-2-pyridyloxy]-2-propanol

Molecular formula: C₁₃H₂₁N₂O₆
Form: Pale yellow viscous oil 1.08 (6H, d, J=6Hz, —CH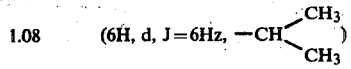)

3.85-4.60 (5H, m, —OCH₂CH(OH)—, —OCH₂CH₂ONO₂)
4.70-5.03 (2H, m, —OCH₂CH₂ONO₂)
6.83 (1H, d.d, J=5Hz, 8Hz, H$_B$)
7.14 (1H, d.d, J=2Hz, 8Hz, H$_A$)
7.78 (1H, d.d, J=2Hz, 5Hz, H$_C$)

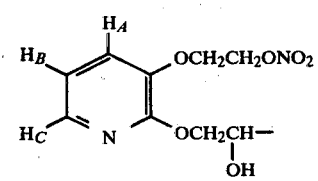

IR spectrum ($\nu_{max}^{liquid\ film}$ cm⁻¹): 1630, 1280 (—NO₂)

EXAMPLE 54

1-iso-Propylamino-3-[3-allyloxy-4-(2-nitratoethoxy)-phenoxy]-2-propanol

Molecular formula: C₁₇H₂₆N₂O₇
Form: Colorless needles
Melting point: 86-87° C.
NMR spectrum (δ, CDCl₃):

1.08 (6H, d, J=6Hz, —CH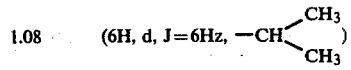)

4.13-4.36 (2H, m, —OCH₂CH₂ONO₂)
4.46-4.66 (2H, m, —OCH₂CH=CH₂)
4.70-4.90 (2H, m, —OCH₂CH₂ONO₂)
5.13-5.62 (2H, m, —CH=CH₂)
5.77-6.30 (1H, m, —CH=CH₂)
6.40 (1H, d.d, J=8Hz, 3Hz, H$_A$)
6.55 (1H, d, J=3Hz, H$_B$)
6.86 (1H, d, J=8Hz, H$_C$)

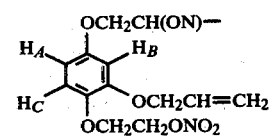

IR spectrum ($\nu_{max}^{KBr}$ cm⁻¹): 1630, 1280 (—NO₂)

EXAMPLE 55

1-iso-Propylamino-3-[3-carbamoyl-4-(2-nitratoethoxy)phenoxy]-2-propanol

Molecular formula: C₁₅H₂₃N₃O₇
Form: Colorless viscous oil
NMR spectrum (δ, CDCl₃)

1.06 (6H, d, J=6Hz, —CH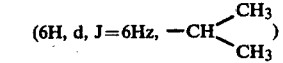)

3.81-4.51 (5H, m, —OCH₂CH(OH)—, —OCH₂CH₂ONO₂)
4.70-5.01 (2H, m, —OCH₂CH₂ONO₂)
6.86 (1H, d, J=9Hz, H of the aromatic ring)
7.04 (1H, d.d, J=3Hz, 9Hz, H of the aromatic ring)
7.71 (1H, d, J=3Hz, H of the aromatic ring)

IR spectrum ($\nu_{max}^{liquid\ film}$ cm⁻¹):

1640 (—CONH₂, —NO₂)
1280 (—NO₂)

EXAMPLE 56

1-iso-Propylamino-3-[4-(2-nitratoethylthio)phenoxy]-2-propanol

Molecular formula: C₁₄H₂₂N₂O₅S
Form: Pale yellow viscous oil
NMR spectrum (δ, CDCl₃):

1.10 (6H, d, J=6Hz, —CH(CH₃)(CH₃))

2.65–3.20 (5H, m, —SCH₂CH₂—, —CH₂NHCH(CH₃)(CH₃))

4.47 (2H, t, J=6Hz, —SCH₂CH₂ONO₂)
6.88 (2H, d, J=9Hz, H of the aromatic ring)
7.43 (2H, d, J=9Hz, H of the aromatic ring)

IR spectrum ($\nu_{max}^{liquid\,film}$ cm⁻¹): 1620, 1288 (—NO₂)

EXAMPLE 57

1-iso-Propylamino-3-[2-(2-nitratoethoxy)-3-nitrophenoxy]-2-propanol

Molecular formula: C₁₄H₂₁N₃O₈
Form: Yellow crystals
Melting point: 105–107° C.
NMR spectrum (δ, CDCl₃):

1.10 (6H, d, J=6Hz, —CH(CH₃)(CH₃))

4.20–4.50 (2H, m, —OCH₂CH₂ONO₂)
4.80–5.00 (2H, m, —OCH₂CH₂ONO₂)
6.80–8.10 (3H, m, H of the aromatic ring)

IR spectrum ($\nu_{max}^{KBr}$ cm⁻¹): 1635, 1285 (—NO₂)

EXAMPLE 58

1-[3-Carbamoyl-4-(2-nitratoethoxy)phenyl]-2-(1-methyl-3-phenylpropyl)aminoethanol Molecular formula: C₂₁H₂₇N₃O₆
Form: Colorless viscous oil
NMR spectrum (δ, CD₃OD)

1.40 (3H, d, J=7Hz, —CHCH₃)

4.40–4.65 (2H, m, —OCH₂CH₂ONO₂)
4.80–5.20 (3H, m, —OCH₂CH₂ONO₂, —CH(OH)CH₂—)
7.20 (1H, d, J=8Hz, H_B)
7.65 (1H, d.d, J=8Hz, 2Hz, H_A)
8.06 (1H, d, J=2Hz, H_C)

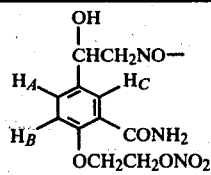

IR spectrum ($\nu_{max}^{liquid\,film}$ cm⁻¹):
1640 (—CONH₂, —NO₂)
1280 (—NO₂)

EXAMPLE 59

1-iso-Propylamino-3-[4-(11-nitratoundecyloxy)-phenoxy]-2-propanol

Molecular formula: C₂₃H₄₀N₂O₆
Form: Colorless crystals
Melting point: 55–56° C.
NMR spectrum (δ, CDCl₃):

1.06 (6H, d, J=6Hz, —CH(CH₃)(CH₃))

4.46 (2H, t, J=6Hz, —CH₂ONO₂)
6.86 (4H, s, H of the aromatic ring)

IR spectrum ($\nu_{max}^{KBr}$ cm⁻¹): 1630, 1280 (—NO₂)

EXAMPLE 60

1-iso-Propylamino-3-[4-(2-nitratoethoxy)-3-sulfamoylphenoxy]-2-propanol

Molecular formula: C₁₄H₂₃N₃O₈S
Form: Colorless viscous oil
NMR spectrum (δ, CDCl₃):

1.09 (6H, d, J=6Hz, —CH(CH₃)(CH₃))

4.75–5.05 (2H, m, —OCH₂CH₂ONO₂)
7.00–7.25 (2H, m, H of the aromatic ring)
7.40–7.60 (1H, m, H of the aromatic ring)

IR spectrum ($\nu_{max}^{liquid\,film}$ cm⁻¹): 1620, 1280 (—NO₂)

EXAMPLE 61

1-iso-Propylamino-3-[4-(3-nitratopropyl)phenoxy]-2-propanol

Molecular formula: C₁₅H₂₄N₂O₅
Form: Colorless crystals
Melting point: 57–58° C.
NMR spectrum (δ, CDCl₃)

1.10 (6H, d, J=6Hz, —CH(CH₃)(CH₃))

4.06 (3H, s, —OCH₂CH(OH)—)
4.53 (2H, t, J=7Hz, —CH₂ONO₂)
7.00 (2H, d, J=9Hz, H of the aromatic ring)
7.30 (2H, d, J=9Hz, H of the aromatic ring)

IR spectrum ($\nu_{max}^{KBr}$ cm⁻¹): 1620, 1290 (—NO₂)

EXAMPLE 62

1-iso-Propylamino-3-[4-(4-nitratobutyl)phenoxy]-2-propanol

Molecular formula: $C_{16}H_{26}N_2O_5$
Form: Colorless needles
Melting point: 52–53° C.
NMR spectrum (δ, CDCl₃)

1.10 (6H, d, J=6Hz, 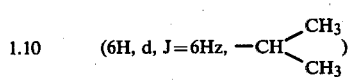)

4.35–4.62 (2H, m, —CH₂ONO₂)
6.95 (2H, d, J=9Hz, H of the aromatic ring)
7.23 (2H, d, J=9Hz, H of the aromatic ring)

IR spectrum ($\nu_{max}^{KBr}$ cm$^{-1}$): 1620, 1280 (—NO₂)

EXAMPLE 63

1-iso-Propylamino-3-[2,6-di(2-nitratoethoxy)phenoxy]-2-propanol

Molecular formula: $C_{16}H_{25}N_3O_{10}$
Form: Pale yellow crystals
Melting point: 65–67° C.
NMR spectrum (δ, CDCl₃)

1.10 (6H, d, J=6Hz, 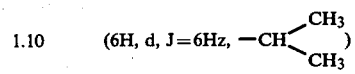)

3.70–4.60 (7H, m, —OCH₂CH(OH)—, —OCH₂CH₂ONO₂)₂)
4.80–5.10 (4H, m, (—OCH₂CH₂ONO₂)₂)
6.60–7.35 (3H, m, H of the aromatic ring)

IR spectrum ($\nu_{max}^{KBr}$ cm$^{-1}$): 1610, 1280 (—NO₂)

EXAMPLE 64

1-iso-Propylamino-3-[2,5]di(2-nitratoethoxy)phenoxy]-2-propanol

Molecular formula: $C_{16}H_{25}N_3O_{10}$
Form: Colorless needles
Melting point: 91–93° C.
NMR spectrum (δ, CDCl₃):

1.10 (6H, d, J=6Hz, 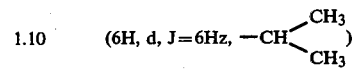)

4.13–4.41 (4H, m, (—OCH₂CH₂ONO₂)₂)
4.70–5.00 (4H, m, (—OCH₂CH₂ONO₂)₂)
6.47 (1H, q, J=9Hz, 3Hz, H$_B$)
6.65 (1H, d, J=3Hz, H$_C$)
6.97 (1H, d, J=9Hz, H$_A$)

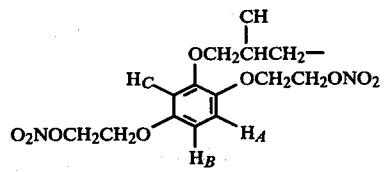

IR spectrum ($\nu_{max}^{KBr}$ cm$^{-1}$): 1618, 1285 (—NO₂)

EXAMPLE 65

1-iso-Propylamino-3-[4-(3-nitratopropylthio)phenoxy]-2-propanol

Molecular formula: $C_{15}H_{24}N_2O_5S$
Form: Colorless viscous oil
NMR spectrum (δ, CDCl₃):

1.09 (6H, d, J=6Hz, 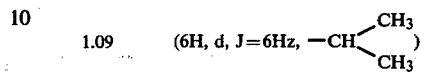)

2.40–3.14 (7H, m, —SCH₂—, —CH₂NHCH(CH₃)₂, —OH)

4.60 (2H, t, J=6Hz, —CH₂ONO₂)
6.93 (2H, d, J=9Hz, H of the aromatic ring)
7.43 (2H, d, J=9Hz, H of the aromatic ring)

IR spectrum ($\nu_{max}^{liquid\ film}$ cm$^{-1}$): 1630, 1280 (—NO₂)

EXAMPLE 66

1-iso-Propylamino-3-[4-(2-nitratoethylsulfinyl)phenoxy]-2-propanol

Molecular formula: $C_{14}H_{22}N_2O_6S$
Form: Pale yellow viscous oil
NMR spectrum (δ, CDCl₃)

1.12 (6H, d, J=6Hz, 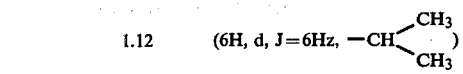)

4.70–4.90 (2H, m, —CH₂ONO₂)
7.15 (2H, d, J=9Hz, H of the aromatic ring)
7.70 (2H, d, J=9Hz, H of the aromatic ring)

IR spectrum ($\nu_{max}^{liquid\ film}$ cm$^{-1}$): 1630, 1280 (—NO₂)

EXAMPLE 67

1-(1,1-Dimethyl-2-hydroxyethylamino)-3-[4-(2-nitratoethoxy)phenoxy]-2-propanol

Molecular formula: $C_{15}H_{24}N_2O_7$
Form: Colorless crystals
Melting point: 77–78.5° C.
NMR spectrum (δ, CDCl₃):

1.10 (6H, s, 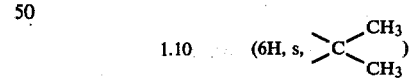)

3.42 (2H, s, —ĊCH₂OH)

4.00 (3H, s, —OCH₂CH(OH)—)
4.13–4.36 (2H, m, —OCH₂CH₂ONO₂)
4.76–4.96 (2H, m, —OCH₂CH₂ONO₂)
6.93 (4H, s, H of the aromatic ring)

IR spectrum ($\nu_{max}^{KBr}$ cm$^{-1}$): 1630, 1260 (—NO₂)

EXAMPLE 68

1-iso-Propylamino-3-[4-(2-nitratoethylamino)phenoxy]-2-propanol

Molecular formula: $C_{14}H_{23}N_3O_5$
Form: Pale yellow viscous oil
NMR spectrum ($\delta$, $CDCl_3$)

1.10 (6H, d, J=6Hz, 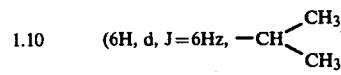)

3.45 (2H, t, J=5Hz, $-NHCH_2CH_2ONO_2$)
4.58 (2H, t, J=5Hz, $-NHCH_2CH_2ONO_2$)
6.42–6.92 (4H, m, H of the aromatic ring)

IR spectrum ($\nu_{max}^{liquid\ film}$ $cm^{-1}$): 1625, 1275 (—$NO_2$)

EXAMPLE 69

1-iso-Propylamino-3-[4-(5-nitrato-n-pentyl)phenoxy]-2-propanol

Molecular formula: $C_{17}H_{28}N_2O_5$
Form: Colorless viscous oil
NMR spectrum ($\delta$, $CDCl_3$):

1.10 (6H, d, J=6Hz, 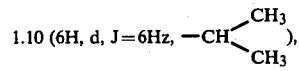), 4.45 (2H, t, J=6Hz, $-CH_2ONO_2$),
6.80 (2H, d, J=9Hz, H of the aromatic ring),
7.10 (2H, d, J=9Hz, H of the aromatic ring)

IR spectrum ($\nu_{max}^{liquid\ film}$ $cm^{-1}$): 1630, 1280 ($NO_2$).

What we claim is:

1. A compound represented by the following formula

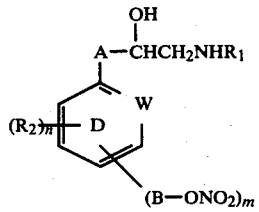

wherein
A represents —O—$CH_2$—
B represents a $C_1$–$C_{11}$ alkylene group bonded to a carbon atom of the aromatic or heteroaromatic ring D either directly or through an —O— or —S— moiety,
W represents a carbon or nitrogen atom,
$R_1$ represents a $C_3$–$C_7$ alkyl group, a hydroxy-$C_1$–$C_6$ alkyl group, or a phenyl- or diphenyl-alkyl group with the alkyl group having 1 to 4 carbon atoms,
$R_2$ represents hydrogen, halogen, OH, $C_1$–$C_4$ alkyl, $NO_2$, $C_1$–$C_4$ alkoxy, acetyl or allyloxy, and when two $R_2$ groups exist, they may be identical or different,
n represents 1 or 2 and m represents 1 or 2; and a pharmaceutically acceptable acid addition salt thereof.

2. A pharmaceutical composition comprising an effective amount, effective for the treatment of angina, hypertension or arrhythmia of a compound or a pharmaceutically acceptable salt thereof, said compound represented by the following formula

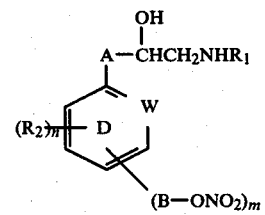

wherein
A represents —O—$CH_2$—
B represents a $C_1$–$C_{11}$ alkylene group bonded to a carbon atom of the aromatic or heteroaromatic ring D either directly or through an —O— or —S— moiety,
W represents a carbon or nitrogen atom,
$R_1$ represents a $C_3$–$C_7$ alkyl group, a hydroxy-$C_1$–$C_6$ alkyl group, or a phenyl- or diphenyl-alkyl group with the alkyl group having 1 to 4 carbon atoms,
$R_2$ represents hydrogen, halogen, OH, $C_1$–$C_4$ alkyl, $NO_2$, $C_1$–$C_4$ alkoxy, acetyl, or allyloxy, and when two $R_2$ groups exist, they may be identical or different,
n represents 1 or 2 and m represents 1 or 2; and a pharmaceutically acceptable diluent or carrier.

3. The pharmaceutical composition of claim 2 wherein the amount of the compound of the formula or its pharmaceutically acceptable acid addition salt is about 0.01 to about 99% by weight based on the total weight of the pharmaceutical composition.

* * * * *